(12) United States Patent
Miner et al.

(10) Patent No.: US 9,402,827 B2
(45) Date of Patent: Aug. 2, 2016

(54) TREATMENT OF GOUT

(75) Inventors: Jeffrey Miner, San Diego, CA (US);
Jean-Luc Girardet, San Diego, CA
(US); Barry D. Quart, Encinitas, CA
(US)

(73) Assignee: ARDEA BIOSCIENCES, INC., San
Diego, CA (US)

( * ) Notice: Subject to any disclaimer, the term of this
patent is extended or adjusted under 35
U.S.C. 154(b) by 474 days.

(21) Appl. No.: 13/637,343

(22) PCT Filed: Mar. 29, 2011

(86) PCT No.: PCT/US2011/030364
§ 371 (c)(1),
(2), (4) Date: Oct. 24, 2012

(87) PCT Pub. No.: WO2011/126852
PCT Pub. Date: Oct. 13, 2011

(65) Prior Publication Data
US 2013/0059868 A1 Mar. 7, 2013

Related U.S. Application Data

(60) Provisional application No. 61/319,014, filed on Mar. 30, 2010.

(51) Int. Cl.
*A61K 31/41* (2006.01)
*A61K 31/165* (2006.01)
*A61K 31/4196* (2006.01)
(52) U.S. Cl.
CPC ............... *A61K 31/41* (2013.01); *A61K 31/165* (2013.01); *A61K 31/4196* (2013.01)

(58) Field of Classification Search
CPC .. A61K 31/41; A61K 31/165; A61K 31/4196
USPC .................................................. 514/383, 384
See application file for complete search history.

(56) References Cited

U.S. PATENT DOCUMENTS

| 7,435,752 | B2 | 10/2008 | Girardet et al. |
| 7,547,680 | B2 | 6/2009 | Kikuchi et al. |
| 7,683,087 | B2 | 3/2010 | Girardet et al. |
| 7,947,721 | B2 | 5/2011 | Girardet et al. |
| 8,003,681 | B2 | 8/2011 | Girardet et al. |
| 8,084,483 | B2 * | 12/2011 | Quart et al. ................. 514/384 |
| 8,106,205 | B2 | 1/2012 | Girardet et al. |

(Continued)

FOREIGN PATENT DOCUMENTS

| CA | 2675443 | 7/2008 |
| CA | 2706858 | 6/2009 |

(Continued)

OTHER PUBLICATIONS

Li, Hong Kong Med. J., 2004:10(4):261-270.*

(Continued)

*Primary Examiner* — San-Ming Hui
(74) *Attorney, Agent, or Firm* — Wilson, Sonsini, Goodrich & Rosati

(57) ABSTRACT

Sodium 2-(5-bromo-4-(4-cyclopropyl-naphthalen-1-yl)-4H-1,2,4-triazol-3-ylthio)acetate is described. In addition, pharmaceutical compositions and uses such compositions for the treatment of a variety of diseases and conditions.

14 Claims, 10 Drawing Sheets

(56) References Cited

U.S. PATENT DOCUMENTS

| | | | |
|---|---|---|---|
| 8,173,690 | B2 | 5/2012 | Gunic et al. |
| 8,193,234 | B2 | 6/2012 | Gunic et al. |
| 8,242,154 | B2 | 8/2012 | Gunic et al. |
| 8,283,369 | B2 | 10/2012 | Quart et al. |
| 8,344,012 | B2 | 1/2013 | Gunic et al. |
| 8,357,713 | B2 | 1/2013 | Quart et al. |
| 8,481,581 | B2 | 7/2013 | Girardet et al. |
| 8,524,754 | B2 | 9/2013 | Zamansky et al. |
| 8,546,436 | B2 | 10/2013 | Galvin et al. |
| 8,546,437 | B2 | 10/2013 | Quart et al. |
| 8,552,043 | B2 | 10/2013 | Girardet et al. |
| 8,633,232 | B2 | 1/2014 | Gunic et al. |
| 8,946,273 | B2 | 2/2015 | Girardet et al. |
| 2006/0189811 | A1 | 8/2006 | Nakamura et al. |
| 2006/0270725 | A1 | 11/2006 | Girardet et al. |
| 2008/0176850 | A1 | 7/2008 | Girardet et al. |
| 2009/0197825 | A1 | 8/2009 | Quart et al. |
| 2010/0056465 | A1 | 3/2010 | Gunic et al. |
| 2010/0056542 | A1 | 3/2010 | Gunic et al. |
| 2010/0081827 | A1 | 4/2010 | Girardet et al. |
| 2010/0160351 | A1 | 6/2010 | Jenkins et al. |
| 2011/0268801 | A1 | 11/2011 | Girardet et al. |
| 2011/0293719 | A1 | 12/2011 | Quart et al. |
| 2012/0122780 | A1 | 5/2012 | De La Rosa et al. |
| 2012/0129903 | A1 | 5/2012 | Zamansky et al. |
| 2012/0164222 | A1 | 6/2012 | Quart et al. |
| 2012/0172405 | A1 | 7/2012 | Galvin et al. |
| 2013/0040963 | A1 | 2/2013 | Gunic et al. |
| 2013/0178484 | A1 | 7/2013 | Miner et al. |
| 2013/0296345 | A1 | 11/2013 | Quart et al. |
| 2013/0331403 | A1 | 12/2013 | Treiber et al. |
| 2013/0345271 | A1 | 12/2013 | Zamansky et al. |
| 2014/0005136 | A1 | 1/2014 | Quart et al. |
| 2014/0128338 | A1 | 5/2014 | Gunic et al. |
| 2014/0171424 | A1 | 6/2014 | Miner |
| 2015/0094284 | A1 | 4/2015 | Girardet et al. |
| 2015/0105410 | A1 | 4/2015 | Treiber et al. |

FOREIGN PATENT DOCUMENTS

| | | |
|---|---|---|
| EP | 2266966 | 12/2010 |
| WO | WO-2006-026356 | 3/2006 |
| WO | WO-2009-070740 | 6/2009 |
| WO | WO-2010-028190 | 3/2010 |
| WO | WO-2011-085009 | 7/2011 |
| WO | WO-2012-092395 | 7/2012 |

OTHER PUBLICATIONS

Ardea Bioscience Company Update. http://www.getfilings.com/sec-filings/091019/Ardea-Biosciences-Inc-DE__8-K/a54060exv99wl.htm (2009).

U.S. Appl. No. 13/704,192 Office Action dated Sep. 16, 2014.

Schumacher, H.R., Jr. "Febuxostat: a Non-Purine, Selective Inhibitor of Xanthine Oxidase for the Management of Hyperuricaemia in Patients with Gout," Expert Opin Investig Drugs 14(7):893-903 (2005).

Burn, C.M. and Wortmann, R.L., "Gout Therapeutics: New Drugs for an Old Disease," Lancet 377(9760): 165-177 (Jan. 8, 2011) (Published Online: Aug. 17, 2010).

Becker, M.A., et al., "Febuxostat Compared with Allopurinol in Patients with Hyperuricemia and Gout," The New England Journal of Medicine 353(23):2450-2461 (Dec. 8, 2005).

PRNewswire, "Ardea Biosciences Reports Positive Results for RDEA594, its Lead Product Candidate for Gout, in Combination with Allopurinol or Febuxostat," Jan. 7, 2009.

PRNewswire, "Ardea Biosciences Reports Positive Results for RDEA594, its Lead Product Candidate for Gout, in Combination with Allopurinol or Febuxostat," Jan. 7, 2010.

PRNewswire, "Ardea Biosciences Announces Positive Top-Line Results From a Phase 2b Study of RDEA594 Given as Monotherapy in the Treatment of Hyperuricemia in Gout Patients," Mar. 31, 2010.

Fleishmann, R., et al. "Lesinurad (RDEA594), A Novel Uricosuric Agent, in Combination with Febuxostat Shows Significant Additive Urate Lowering Effects in Gout Subjects with 100% Response Achieved for all Combination Dose Regimens," Annual European Congress of Rheumatology EULAR, London, May 25-28, 2011.

Kerr, B., et al. "Pharmacokinetics, Efficacy and Safety of Lesinurad, A Novel URAT1 Inhibitor, In Individuals with Mild to Moderate Renal Impairment, " American College of Rheumatology Annual General Meeting, Nov. 5-9, 2011, Chicago.

Kerr, B., et al. "Pharmacokinetics and Serum Urate Lowering Effect of RDEA594, A Novel URAT1 Inhibitor, In Gout Patients and Subjects with Varying Degrees of Renal Impairment," ASCPT American Society for Clinical Pharmacology and Therapeutics Annual Meeting, Dallas, Mar. 2-5, 2011.

Lasko, B., et al. "RDEA594, a Novel Uricosuric Agent, Significantly Reduced Serum Urate Levels and Was Well Tolerated in a Phase 2a Pilot Study in Hyperuricemic Gout Patients," ACR-ARHP Annual Scientific Meeting, Oct. 16-21, 2009, Philadelphia, CA USA.

Perez-Ruiz, F., et al. "Efficacy and Safety of Lesinurad (RDEA594), a Novel URAT1 Inhibitor, in Combination with Allopurinol in Gout Patients with an Inadequate Response to Allopurinol: Results from a Randomized, Blinded. Placebo-Controlled, Phase 2B Extension Study," Annual European Congress of Pheumatology EULAR, Berlin, Jun. 6-9, 2012.

Perez-Ruiz, F., et al. "Efficacy and Safety of Lesinurad (RDEA594), A Novel Uricosuric Agent, Given in Combination with Allopurinol in Allopurinol-Refractory Gout Patients: Randomized, Double-Blind Placebo-Controlled, Phase 2B Study [Preliminary Results]" Annual European Congress of Rheumatology EULAR 2011, May 25-28, 2011, London.

Perez-Ruiz, F., et al. "Efficacy and Safety of a Range of Doses of RDEA594, a Novel Uricosuric Agent, as Monotherapy in Gout Patients: Randomized, Double-Blind, Placebo-Controlled, Phase 2 Experience," Annual European Congress of Rheumatology EULAR 2010, Jun. 16-19, 2010, Rome.

Perez-Ruiz, F., et al. "Efficacy and Safety of RDEA594, a Novel Uricosuric Agent, as Combination Therapy with Allopurinol in Gout Patients: Randomized, Double-Blind, Placebo-Controlled, Phase 2 Experiences," Annual European Congress of Rheumatology EULAR 2010, Rome, Italy, Jun. 16-19, 2010.

Shen, Z., et al. "RDEA594, A Novel Uricosuric Agent, Shows Significant Additive Activity in Combination with Allopurinol in Gout Patients" ASCPT American Society of Clinical Pharmacology and Therapeutics Annual Meeting, Dallas, Mar. 2-5, 2011.

Sundy, J., et al. "Efficacy and Safety of Lesinurad (RDEA594), A Novel Given in Combination with Allopurinol in Allopurinol-Refractory Gout Patients: Preliminary Results from the Randomized, Blinded, Placebo-Controlled, Phase 2B Extension Study," American Collage of Pheumatology Annual General Meeting, Nov. 9-11, 2011, Chicago.

Tan, P.K., et al. "Lesinurad (RDEA594), A Investigational Uricosuric Agent for Hyperuricemia and Gout, Blocks OAT4 Transport, Mechanism of Hydrocholorothiazide-Dependant Hyperuricemia," Annual European Congress of Rheumatology EULAR, London, May 25-28, 2011.

Yang, X., et al. "Evaluation of Drug-Drug Interaction Potential Between RDEA594, Allopurinol and Febuxostat in Preclinical Species" 2009 ACR-ARHP Annual Scientific Meeting, Oct. 16-21, 2009, Philadelphia, PA, USA.

Yeh, L., et al. "RDEA594, a Novel Uricosuric Agent, Shows Impressive Reductions in Serum Urate Levels as a Monotherapy and Substantial Additive Activity in Combination with Febuxostat in Normal Healthy Volunteers," Annaul European Congress of Rheumatology EULAR 2010, Rome, Italy, Jun. 16-19, 2010.

Yeh, L., et al. "RDEA594, a Potential Uric Acid Lowering Agent through Inhibition of Uric Acid Reuptake, Shows Better Pharmacokinetics than its Prodrug RDEA806," 2008 ACR/ARHP Annual Scientific Meeting, Oct. 24-29, 2008, San Francisco, CA, USA.

Yeh, L., et al. "A Novel URAT1 Inhibitor, Shows Significant Additive Urate Lowering Effects in Combination with Febuxostat in Both

(56) References Cited

OTHER PUBLICATIONS

Healthy Subjects and and Gout Patients," ASCPT American Society for Clinical Pharmacology and Therapeutics Annual Meeting, Dallas, Mar. 2-5, 2011.

Yeh, L., et al., "Lesinurad (RDEA594), A Novel URAT1 Inhibitor, Shows Additive Serum Urate Lowering Effects in Combination with Xanthine Oxidase Inhibitor Febuxostat" International Society for the Study of Xenobiotics, 4th Asia Pacific ISSX Meeting, Apr. 22-25, 2011.

Yeh, L.T., et al. "Mode of Action of RDEA594 as a Uric Acid Lowering Agent in Humans Following Multiple Doses of its Prodrug, RDEA806," Annual European Congress of Rheumatology EULAR 2008, Paris, France, Jun. 11-14, 2008.

Yeh, L.T., et al. "Safety, Pharmacokinetics, and Serum Uric Acid Lowering Effect of RDEA594, A Novel, Uricosuric Agent, in Healthy Volunteers," Annual European Congress of Rheumatology EULAR 2009, Copenhagen, Denmark, Jun. 10-13, 2009.

Yeh, L.-T., et al. "RDEA594: A Potent URAT1 Inhibitor Without Affecting Other Important Renal Transporters, OAT1 and OAT3," Annual European Congress of Rheumatology EULAR 2009, Copenhagen, Denmark, Jun. 10-13, 2009.

PCT/US11/040398 International Search Report and Written Opinion dated Nov. 1, 2011.

PCT/US11/030364 International Search Report and Written Opinion dated Nov. 10, 2011.

Becker et al. Febuxostat compared with allopurinol in patients with hyperuricemia and gout. N Engl J Med 353(23):2450-2461 (2005).

U.S. Appl. No. 13/704,192 Office Action dated May 21, 2015.

U.S. Appl. No. 13/879,373 Office Action dated May 8, 2015.

Co-pending U.S. Appl. No. 14/939,963, filed Nov. 12, 2015.

U.S. Appl. No. 13/879,373 Office Action dated Oct. 7, 2015.

EDGE. Lactose Monohydrate Monograph. Handbook of Pharmaceutical Excipient. 6th ed. pp. 364-369 (2009).

U.S. Appl. No. 13/879,373 Office Action dated May 2, 2016.

* cited by examiner

A:

B:

A:

B:

A:

\* P< 0.05

B:

A:

B:

TREATMENT OF GOUT

CROSS-REFERENCE

This application is filed pursuant to 35 U.S.C. §371 as a United States National Phase Application of International Application Ser. No. PCT/US11/030364, filed Mar. 29, 2011, which claims priority to U.S. Provisional Application No. 61/319,014, filed Mar. 30, 2010, all of which are incorporated herein by reference in their entirety.

FIELD OF THE INVENTION

The present invention relates to the treatment of gout while substantially reducing the duration and frequency of gout flares associated with reductions of uric acid levels.

BACKGROUND OF THE INVENTION

Gout is associated with elevated levels of uric acid that crystallize and deposit in joints, tendons, and surrounding tissues. Gout is marked by recurrent attacks of red, tender, hot, and/or swollen joints.

SUMMARY OF THE INVENTION

The treatment of gout typically involves the reduction of serum uric acid levels. However, gout flares are associated with the reduction of uric acid levels. Drugs such as colchicine can reduce the pain associated with gout flares while a patient's serum uric acid levels are being reduced, however, colchicine is associated with several undesired side effects, including gastrointestinal disorders.

Accordingly, described herein are methods, compositions and dosing regimens for reducing serum uric acid levels while providing for a concomitant reduction in the intensity and duration of gout flares associated with other gout medications. Furthermore, described herein are methods, compositions and dosing regimens for weaning a patient off of co-administered colchicine; such weaning includes lower doses of colchicine and less time on colchicine relative to other gout medications.

One embodiment provides a method of treating gout comprising co-administration of 2-(5-bromo-4-(4-cyclopropyl-naphthalen-1-yl)-4H-1,2,4-triazol-3-ylthio)acetate, or a pharmaceutically acceptable salt thereof, and colchicine to a subject, wherein said method provides greater mean gout flare reduction than co-administration of colchicine and therapeutic agent that is not a dual inhibitor of URAT1 and an inflammasome.

Another embodiment provides the method wherein the total dosage of colchicine administered during co-administration with 2-(5-bromo-4-(4-cyclopropylnaphthalen-1-yl)-4H-1,2,4-triazol-3-ylthio)acetate, or a pharmaceutically acceptable salt thereof, is at least 50% less than the total dosage of colchicine co-administered with a therapeutic agent that is not a dual inhibitor of URAT1 and an inflammasome.

Another embodiment provides the method wherein the amount of time that colchicine is co-administered with 2-(5-bromo-4-(4-cyclopropylnaphthalen-1-yl)-4H-1,2,4-triazol-3-ylthio)acetate, or a pharmaceutically acceptable salt thereof, is at least one week less than when colchicine is co-administered with a therapeutic agent that is not a dual inhibitor of URAT1 and an inflammasome.

One embodiment provides a method of reducing the duration of gout flares comprising administration of a pharmaceutical composition comprising 2-(5-bromo-4-(4-cyclopropyl-naphthalen-1-yl)-4H-1,2,4-triazol-3-ylthio)acetate, or a pharmaceutically acceptable salt thereof, to a subject, wherein the mean duration of the gout flares in a patient undergoing uric acid level reduction is less than four days. Another embodiment provides the method, wherein the mean duration of the gout flares is less than three days. Another embodiment provides the method wherein the mean duration of the gout flares is less than two days.

One embodiment provides a method for treating gout comprising administration to a patient in need a therapeutic agent that is a dual inhibitor of URAT1 and inflammasome. Another embodiment provides the method wherein the dual inhibitor of URAT1 and inflammasome is 2-(5-bromo-4-(4-cyclopropylnaphthalen-1-yl)-4H-1,2,4-triazol-3-ylthio)acetate, or a polymorph thereof, or a pharmaceutically acceptable salt of 2-(5-bromo-4-(4-cyclopropylnaphthalen-1-yl)-4H-1,2,4-triazol-3-ylthio)acetate or a polymorph thereof.

One embodiment provides a method of reducing monosodium urate induced inflammation comprising administering a pharmaceutical composition comprising a pharmaceutical agent having both uricosuric and anti-inflammatory activity. Another embodiment provides the method wherein the pharmaceutical agent is a URAT1 inhibitor with anti-inflammatory activity. Another embodiment provides the method wherein the pharmaceutical agent is 2-(5-bromo-4-(4-cyclopropylnaphthalen-1-yl)-4H-1,2,4-triazol-3-ylthio)acetate, or a pharmaceutically acceptable salt thereof.

In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 750 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 600 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 500 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 400 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 200 mg.

In another embodiment is provided the method wherein the daily dose is administered orally. In another embodiment is provided the method wherein the daily dose is administered in the morning. In another embodiment is provided the method wherein the daily dose is administered with food.

Another embodiment provides the above listed methods of reducing the duration of gout flares further comprising administration of a second serum uric acid lowering agent. In another embodiment is provided the method wherein the second serum uric acid lowering agent is a xanthine oxidase inhibitor. In another embodiment is provided the method wherein the xanthine oxidase inhibitor is febuxostat or allopurinol.

INCORPORATION BY REFERENCE

All publications and patent applications mentioned in this specification are herein incorporated by reference for the purposes cited.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A illustrates plasma extravasation value, FIG. 6B exudate volume, and FIG. 6C total white blood cell count.

DETAILED DESCRIPTION OF THE INVENTION

Figure 1:
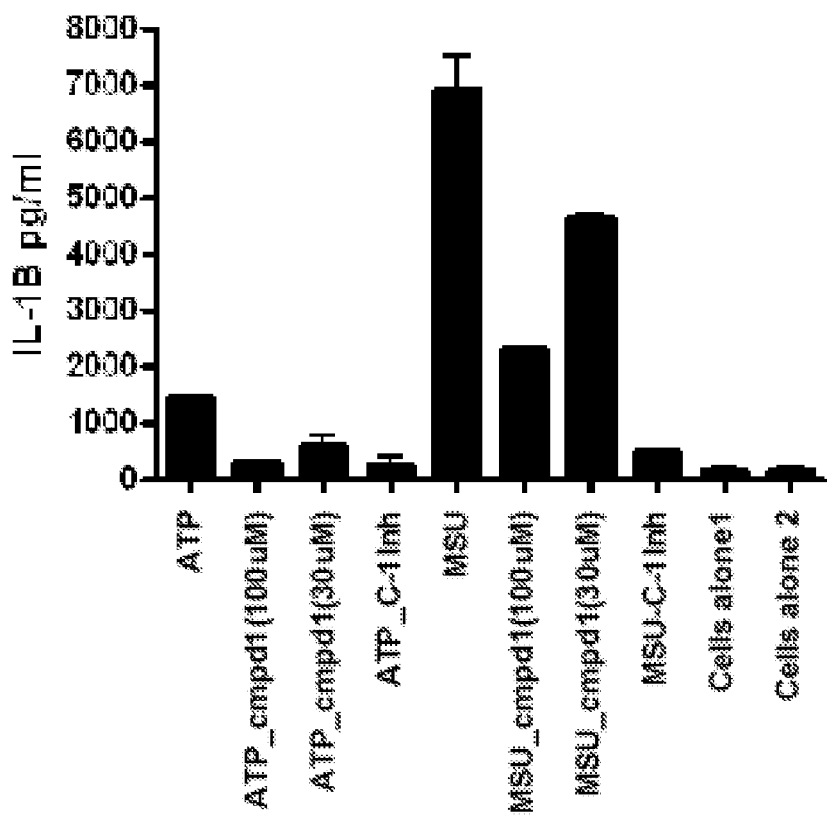
FIG. 1 illustrates the effect of Lesinurad on IL-1β release within 1 hour of stimulation with ATP (5 mM) or 1 μg MSU (monosodium urate) crystals (compd1=Lesinurad; C-1inh=caspase-1 inhibitor).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The treatment of gout typically involves the reduction of serum uric acid levels. However, gout flares are associated with the reduction of uric acid levels. Drugs such as colchicine can reduce the pain associated with gout flares while a patient's serum uric acid levels are being reduced, however, colchicine is associated with several undesired side effects, including gastrointestinal disorders.

Accordingly, described herein are methods, compositions and dosing regimens for reducing serum uric acid levels while providing for a concomitant reduction in the intensity and duration of gout flares associated with other gout medications. Furthermore, described herein are methods, compositions and dosing regimens for weaning a patient off of co-administered colchicine; such weaning includes lower doses of colchicine and less time on colchicine relative to other gout medications.

One embodiment provides a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and a second therapeutic agent for the treatment of gout (and/or symptoms thereof). In specific embodiments, the second therapeutic agent for the treatment of gout (and/or symptoms thereof) is an NSAID, steroid, or colchicine. In other embodiments, the second therapeutic agent for the treatment of gout (and/or symptoms thereof) is any therapeutic agent described herein for the treatment of gout (and/or symptoms thereof). In some embodiments, the second therapeutic agent for the treatment of gout (and/or symptoms thereof) is an agent that treats, reduces the intensity of, or reduces the duration of gout symptoms (e.g., effects associated with gout other than uric acid concentrations). In specific embodiments, the second agent is colchicine. In certain embodiments, provided herein is a method of treating gout in a subject in need thereof, the method comprising co-administering 2-(5-bromo-4-(4-cyclopropylnaphthalen-1-yl)-4H-1,2,4-triazol-3-ylthio)acetate, or a pharmaceutically acceptable salt thereof, and colchicine to a subject. In specific embodiments, provided herein is a method that provides greater mean gout flare reduction (intensity, incidences and/or duration) than co-administration of colchicine (e.g., a similar amount of colchicine) and therapeutic agent that is not a dual inhibitor of URAT1 and an inflammasome. In some embodiments, a therapy described herein is administered to a subject that has received previous gout therapy comprising the administration of the second agent and a third therapeutic agent for the treatment of gout (e.g., wherein the third therapeutic agent is not an inhibitor of URAT1, is not an inflammasome, or both). In specific embodiments, the amount of second agent is reduced by at least 25%, at least 40%, at least 50%, at least 60%, at least 75%, or any other suitable amount when compared to the amount of second agent that was administered with the third therapeutic agent.

Another embodiment provides the method wherein the total dosage of colchicine administered during co-administration with 2-(5-bromo-4-(4-cyclopropylnaphthalen-1-yl)-4H-1,2,4-triazol-3-ylthio)acetate, or a pharmaceutically acceptable salt thereof, is at least 50% less than the total dosage of colchicine co-administered with a therapeutic agent that is not a dual inhibitor of URAT1 and an inflammasome (e.g., at least 50% less than the total dosage of colchicine that would be required to provide a similar or identical effect when co-administered with a therapeutic agent that is not a dual inhibitor of URAT1 and an inflammasome; e.g., a similar effect being one wherein the effect is at least 80% similar, at least 90% similar, or the like). In certain embodiments, the daily dosage of colchicine is less than 3 mg, less than 1.5 mg, less than 1.2 mg, less than 1 mg, less than 0.7 mg, less than 0.5 mg, less than 0.3 mg, or the like. In some embodiments, the initial dosage of colchicine is less than 1.2 mg, less than 1 mg, less than 0.7 mg, less than 0.5 mg, less than 0.3 mg, or the like. In certain embodiments, the dosage of colchicine subsequent to the initial dose is less than 0.6 mg, less than 0.5 mg, less than 0.3 mg, less than 0.15 mg, or the like.

Another embodiment provides the method wherein the amount of time that colchicine is co-administered with 2-(5-bromo-4-(4-cyclopropylnaphthalen-1-yl)-4H-1,2,4-triazol-3-ylthio)acetate, or a pharmaceutically acceptable salt thereof, is at least one week less than when colchicine is co-administered with a therapeutic agent that is not a dual inhibitor of URAT1 and an inflammasome (e.g., at least one week less than the total dosage of colchicine that would be required to provide a similar or identical effect when co-administered with a therapeutic agent that is not a dual inhibitor of URAT1 and an inflammasome; e.g., a similar effect being one wherein the effect is at least 80% similar, at least 90% similar, or the like).

In some embodiments, provided herein is a method of treating gout comprising administering to an individual in need thereof a therapeutically effective amount of 2-(5-bromo-4-(4-cyclopropylnaphthalen-1-yl)-4H-1,2,4-triazol-3-ylthio)acetate, or a pharmaceutically acceptable salt thereof. In specific embodiments, the therapeutically effective amount of 2-(5-bromo-4-(4-cyclopropylnaphthalen-1-yl)-4H-1,2,4-triazol-3-ylthio)acetate, or a pharmaceutically acceptable salt thereof is sufficient to reduce the incidences of, reduce the duration of, and/or reduce the severity or intensity of the gout symptoms (e.g., flares). In some embodiments, the method further comprises reducing the amount of a second therapeutic agent for the treatment of gout, (and/or symptoms thereof), administered to the subject. In some embodiments, the second therapeutic agent is an NSAID, steroid, or colchicine. In specific embodiments, the second agent is colchicine. In specific embodiments, the amount of second agent is reduced by at least 25%, at least 40%, at least 50%, at least 60%, at least 75%, or any other amount to provide efficacious gout (and/or gout symptom) therapy.

One embodiment provides a method of reducing the duration of gout flares comprising administration of a pharmaceutical composition comprising 2-(5-bromo-4-(4-cyclopropyl-naphthalen-1-yl)-4H-1,2,4-triazol-3-ylthio)acetate, or a pharmaceutically acceptable salt thereof, to a subject, wherein the mean duration of the gout flares in a patient undergoing uric acid level reduction is less than four days. Another embodiment provides the method, wherein the mean duration of the gout flares is less than three days. Another embodiment provides the method wherein the mean duration of the gout flares is less than two days.

One embodiment provides a method for treating gout comprising administration to a patient in need a therapeutic agent that is a dual inhibitor of URAT1 and inflammasome. Another embodiment provides the method wherein the dual inhibitor of URAT1 and inflammasome is 2-(5-bromo-4-(4-cyclopropylnaphthalen-1-yl)-4H-1,2,4-triazol-3-ylthio)acetate, or a polymorph thereof, or a pharmaceutically acceptable salt of 2-(5-bromo-4-(4-cyclopropylnaphthalen-1-yl)-4H-1,2,4-triazol-3-ylthio)acetate or a polymorph thereof.

One embodiment provides a method of reducing monosodium urate induced inflammation comprising administering a pharmaceutical composition comprising a pharmaceutical agent having both uricosuric and anti-inflammatory activity. Another embodiment provides the method wherein the pharmaceutical agent is a URAT1 inhibitor with anti-inflammatory activity. Another embodiment provides the method wherein the pharmaceutical agent is 2-(5-bromo-4-(4-cyclopropylnaphthalen-1-yl)-4H-1,2,4-triazol-3-ylthio)acetate, or a pharmaceutically acceptable salt thereof.

In some embodiments a method described herein provides a daily dose of 2-(5-bromo-4-(4-cyclopropylnaphthalen-1-yl)-4H-1,2,4-triazol-3-ylthio)acetate, or a pharmaceutically acceptable salt thereof, is about 10 mg to about 2 g, about 50 mg to about 1 g, about 200 mg to about 800 mg, about 200 mg to about 600 mg, or any other suitable therapeutically effective amount. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 750 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 600 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 500 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 400 mg. In another embodiment is provided the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 200 mg.

In another embodiment is provided the method wherein the daily dose is administered orally. In another embodiment is provided the method wherein the daily dose is administered in the morning. In another embodiment is provided the method wherein the daily dose is administered with food.

Another embodiment provides the above listed methods of reducing the duration of gout flares further comprising administration of a second serum uric acid lowering agent. In another embodiment is provided the method wherein the second serum uric acid lowering agent is a xanthine oxidase inhibitor. In another embodiment is provided the method wherein the xanthine oxidase inhibitor is febuxostat or allopurinol.

Gout

Gout is a painful form of arthritis caused by high uric acid in the blood (hyperuricemia). As serum uric acid (sUA) levels increase, so does the risk of having gout and painful flares. Decreasing uric acid to a level of less than 6 mg/dL has been shown to be effective for management of gout over the long-term.

According to the National Health and Nutrition Examination Survey III, 1988-1994, an estimated 5.1 million people in the United States suffer from gout. Gout is the most common form of inflammatory arthritis in men. Gout affects approximately 3 times as many men as women, and men are more likely than women to have gout at all ages. Racial and ethnic differences are not as distinct among patients in the US, though African Americans aged 45 years or older are more likely to have gout than Caucasians in the same age group.

Gout flares occur when excess uric acid forms crystals, causing inflammation in the joints that leads to swelling and pain. Flares happen most often in the toes, but can happen in hands, elbows, and knees. Gout flares often occur without warning and can cause joint swelling, severe pain, tenderness, redness, and heat. Over time, gout flares become more frequent and of greater duration.

Acute gout is caused by an inflammatory response to monosodium urate monohydrate (MSUM) crystal formation—a temperature-dependent phenomenon, which can occur under conditions of elevated serum urate concentration. Gout flare is known as one of the most painful conditions in rheumatology, with pain intensity comparable to childbirth or long bone fractures. The condition regularly interrupts sleep, inhibits walking, and interferes with work and leisure activities.

Serum urate, produced when purines are metabolized, is eliminated from the body in the form of uric acid. Uric acid may have a significant physiological function, acting as an antioxidant, a role in which it is as effective as ascorbate. However, when the balance of purine nucleotide synthesis, breakdown and recycling, and elimination becomes unbalanced, hyperuricemia may result.

The development of hyperuricemia is straightforward: uric acid builds up in the blood when the body increases its production of uric acid, or the kidneys do not eliminate it efficiently, or both. Overproduction is responsible for 10% of cases of primary gout; underexcretion for 90%.

Production may increase through endogenous (cell turnover and metabolism) and/or exogenous (dietary) factors.

Reduced elimination suggests a renal cause because most uric acid is eliminated via the kidneys. (Enteric elimination is the next most significant means of elimination, and it can increase in response to hyperuricemia.) Genetic factors may play a role for individuals with hyperuricemia and reduced renal clearance of uric acid. Most subjects with gout have lower clearance rates for uric acid, which may be measured directly or as a ratio of urate to inulin clearance (Curate/Cinulin ratio). However, most gout and hyperuricemia patients show no other renal function abnormality.

Though 90% of primary gout cases are triggered by difficulties in urate elimination, the exact mechanism behind lower uric acid clearance rates has not been established. Known factors that may affect urate clearance include the volume of urine flow (excretion is increased by >25% if urine flow is doubled), the level of estrogens (as evidenced by lower serum uric acid concentrations in women before menopause and in children), surgery, and autonomic nervous system function.

Secondary gout can also be attributed to a reduction in the glomerular filtration rate causing a decrease in the excretion of uric acid by the kidney. This can be seen in certain kidney disorders or with medications such as diuretics that interfere with urate excretion.

Gout Flares

The serum urate saturation point is approximately 6.8 mg/dL. Although several biochemical factors impact whether an individual experiences a flare at this point. Risk for the development of gout symptoms increases steadily at concentrations higher than 6 mg/dL. In a patient with hyperuricemia, urate can crystallize as monosodium urate monohydrate (MSUM) and may form deposits in the synovial membrane. An acute gout attack can occur when there is a marked inflammatory response to these crystal deposits.

In broad terms, gout attacks are symptoms of the inflammatory response to monosodium urate crystal deposition. Supersaturation of serum urate is the underlying cause, but not sufficient in and of itself to cause precipitation. Similarly, the presence of crystals alone may be insufficient to elicit an inflammatory response.

Asymptomatic patients may have crystals in the synovial fluid and neutrophils within the synovium—diagnostic clinical signs of gout. Additionally, microtophi have been identified in areas of the synovium during the early stages of gout attacks. These observations are consistent with a continuum of inflammatory response between intercritical periods and acute attacks in chronic gout.

The inflammatory response may be initiated when microcrystals shed from microtophi adjacent to the joint space and enter the synovial fluid. In addition to their location, the size of the crystals may be a significant factor. New microcrystals that form and those that break off from larger crystals appear to be essential to the process. This observation may also explain why aggressive antihyperuricemic therapy may trigger a mobilization flare: it can cause larger crystals to dissolve and release microcrystals. Thus, prophylactic treatment with anti-inflammatory drugs has been recommended for 6 months or longer after the start of antihyperuricemic therapy, while urate levels are in flux.

Many biochemical mediators are involved in the inflammatory response. Monocytes play a large role, releasing proinflammatory cytokines and attracting neutrophils to the site, thus amplifying the response. Phagocytes resident within the synovium may be insufficient to trigger an immune response to microcrystals. However, the entry of new monocytes and neutrophils may shift the immune balance, leading to the gout flare.

Treatment of Gout

NSAIDs

NSAIDS are the usual first line treatment for gout with no significant difference between agents in effectiveness. Improvement may be seen within 4 hours. They however are not recommended in those with certain other health problems such as gastrointestinal bleeding, renal failure, or heart failure. While indomethacin is historically the most commonly used NSAID, due to concerns of side effects and no evidence of greater benefit, an alternative like ibuprofen may be preferred. For those at risk of gastric irritation from NSAIDs, an additional proton pump inhibitor may be given. NSAIDs include but are not limited to aminoarylcarboxylic acid derivatives such as enfenamic acid, etofenamate, flufenamic acid, isonixin, meclofenamic acid, mefenamic acid, niflumic acid, talniflumate, terofenamate, and tolfenamic acid; arylacetic acid derivatives such as aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac isoxepac, lonazolac, metiazinic acid, mofezolac, oxametacine, pirazolac, proglumetacin, sulindac, tiaramide, tolmetin, tropesin, and zomepirac; arylbutyric acid derivatives such as bumadizon, butibufen, fenbufen, xenbucin; arylcarboxylic acids such as clidanac, ketorolac, tinoridine; arylpropionic acid derivatives such as alminoprofen, benoxaprofin, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprofin, pirprofen, pranoprofen, protizinic acid, suprofen, tiaprofenic acid, ximoprofen, and zaltoprofen; pyrazoles such as difenamizole, and epirozole; pyrazolones such as apazone, benzpiperylon, feprazone, mofebutazone, morazone, oxyphenbutazone, phenylbutazone, pipebuzone, propyphenazone, prostaglandins, ramifenazone, suxibuzone, and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphtyl salicylate, olsalazine, parsalmide, phenyl acetylsalicylate, phenyl salicylate, salacetamide, salicylamide o-acetic acid, salicylsulfuric acid, salsalate, sulfasalazine; thiazinecarboxamides such as ampiroxicam, droxicam, isoxicam, lomoxicam, piroxicam, and tenoxicam; cyclooxygenase-II inhibitors ("COX-II") such as Celebrex (Celecoxib), Vioxx, Relafen, Lodine, and Voltaren and others, such as epsilon-acetamidocaproic acid, s-adenosylmethionine, 3-amino-4-hydroxybutytic acid, amixetrine, bendazac, benzydamine, α-bisabolol, bucololome, difenpiramide, ditazol, emorfazone, fepradinol, guaiazulene, nabumetone, nimesulide, oxaceprol, paranyline, perisoxal, proquazone, tenidap and zilenton; sleep aids including but not limited to a benzodiazepine hypnotic, non-benzodiazepine hypnotic, antihistamine hypnotic, antidepressant hypnotic, herbal extract, barbiturate, peptide hypnotic, triazolam, brotizolam, loprazolam, lormetazepam, flunitrazepam, flurazepam, nitrazepam, quazepam, estazolam, temazepam, lorazepam, oxazepam, diazepam, halazepam, prazepam, alprazolam, chlordiazepoxide, clorazepate, an imidazopyridine or pyrazolopyrimidine hypnotic, zolpidem or zolpidem tartarate, zopiclone, eszopiclone, zaleplon, indiplone, diphenhydramine, doxylamine, phenyltoloxamine, pyrilamine, doxepin, amtriptyline, trimipramine, trazodon, nefazodone, buproprion, bupramityiptyline, an herbal extract such as valerian extract or amentoflavone, a hormone such as melatonin, or gabapeptin.

Steroids

Glucocorticoids have been found to be equally effective to NSAIDs and may be used if contraindications exist for NSAIDs. Intra-articular steroids have also been found to be effective however the risk of concurrent joint infection must be ruled out.

Colchicine

Colchicine is an alternative for those unable to tolerate NSAIDs. Its side effects (primarily gastrointestinal upset) has decreased its usage. Gastrointestinal upset however depends on the dose and the risk can be decreased by using smaller yet still effective doses. Colchicine may interact with other commonly prescribed drugs such as atorvastatin and erythromycin among others. When administered in the formulation marketed as COLCRYS (cholchicine, USP), the recommended dose for the prophylaxis of gout flares is 0.6 mg once or twice daily. For the treatment of gout flares the recommended dose is 1.2 mg at first indication of a flare followed by 0.6 mg one hour later.

Agents which have found use in the treatment of gout are P2x receptor inhibitors, reactive oxygen species inhibitors, toll like receptor antagonists, IL1 inhibitors—anakinra, rilonacept, TNF blockers—enbrel etc., glucocorticoids prednisone, prednisolone, triamcinolone, dexamethasone, inflammasome inhibitors, caspase inhibitors, NSAIDS—celecoxib, Ibuprofen, naproxen, fenbufen, fenoprofen, flurbiprofen, ketoprofen, tiaprofenic acid, azapropazone, diclofenac, diflunisal, etodolac, indomethacin (indometacin), ketorolac, mefenamic, meloxicam, nabumetone, phenylbutazone, piroxicam, sulindac, tenoxicam, tolfenamic acid, hydroxychloroquine (Plaquenil) or chloroquine (Aralen), leflunomide (Arava), methotrexate, sulfasalazine azulfidine, Abatacept (Orencia), Adalimumab (Humira), Anakinra (Kineret), Etanercept (Enbrel), Infliximab (Remicade), Rituximab (Rituxan).

URAT1

URAT1 is a urate transporter and urate-anion exchanger which regulates the level of urate in the blood. This protein is an integral membrane protein primarily found in kidney.

Inflammasome

The inflammasome is responsible for activation of inflammatory processes, and has been shown to induce cell pyroptosis, a process of programmed cell death distinct from apoptosis. The inflammasome is a multiprotein complex consisting of caspase 1, PYCARD, a NALP and sometimes caspase 5 or caspase 11. The exact composition of an inflammasome depends on the activator which initiates inflammasome assembly i.e. dsRNA will trigger one inflammasome composition whereas asbestos will assembly a different variant. The inflammasome promotes the maturation of inflammatory cytokines interleukin 1-β and interleukin 18.

The present invention relates to methods for treating or preventing diseases, comprising administering an effective amount of sodium 2-(5-bromo-4-(4-cyclopropylnaphthalen-1-yl)-4H-1,2,4-triazol-3-ylthio)acetate.

Sodium 2-(5-bromo-4-(4-cyclopropylnaphthalen-1-yl)-4H-1,2,4-triazol-3-ylthio)acetate Sodium 2-(5-bromo-4-(4-cyclopropylnaphthalen-1-yl)-4H-1,2,4-triazol-3-ylthio)acetate is known to decrease uric acid levels, (see for example US 2009-0197825, U.S. patent application Ser. No. 12/553,844 and U.S. patent application Ser. No. 12/554,719). Details of clinical studies involving sodium 2-(5-bromo-4-(4-cyclopropylnaphthalen-1-yl)-4H-1,2,4-triazol-3-ylthio)acetate have been described in U.S. provisional patent application 61/252,530, U.S. provisional patent application 61/252,537 and U.S. provisional patent application 61/265,240.

Uric acid is the result of the oxidation of xanthine. Disorders of uric acid metabolism include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

DEFINITIONS

The term "subject", as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "effective amount", "therapeutically effective amount" or "pharmaceutically effective amount" as used herein, refer to an amount of at least one agent or compound being administered that is sufficient to treat or prevent the particular disease or condition. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

Modulating URAT-1 Activity

The invention also relates to methods of modulating URAT-1 activity by contacting URAT-1 with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to modulate the activity of URAT-1. Modulate can be inhibiting or activating URAT-1 activity. In some embodiments, the invention provides methods of inhibiting URAT-1 activity by contacting URAT-1 with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to inhibit the activity of URAT-1. In some embodiments, the invention provides methods of inhibiting URAT-1 activity in a solution by contacting said solution with an amount of a polymorphic, crystalline or mesophase form of sodium 2-(5-bromo-4-(4-cyclopropylnaphthalen-1-yl)-4H-1,2,4-triazol-3-ylthio)acetate, as described herein sufficient to inhibit the activity of URAT-1 in said solution. In some embodiments, the invention provides methods of inhibiting URAT-1 activity in a cell by contacting said cell with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to inhibit the activity of URAT-1 in said cell. In some embodiments, the invention provides methods of inhibiting URAT-1 activity in a tissue by contacting said tissue with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to inhibit the activity of URAT-1 in said tissue. In some embodiments, the invention provides methods of inhibiting URAT-1 activity in blood by contacting the blood with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to inhibit the activity of URAT-1 in blood. In some embodiments, the invention provides methods of inhibiting URAT-1 activity in plasma by contacting the plasma with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to inhibit the activity of URAT-1 in plasma. In some embodiments, the invention provides methods of inhibiting URAT-1 activity in an animal by contacting said animal with an amount of a polymorphic, crystalline or mesophase form of sodium 2-(5-bromo-4-(4-cyclopropylnaphthalen-1-yl)-4H-1,2,4-triazol-3-ylthio)acetate, as described herein sufficient to inhibit the activity of URAT-1 in said animal. In some embodiments, the invention provides methods of inhibiting URAT-1 activity in a mammal by contacting said mammal with an amount of a polymorphic, crystalline or mesophase form of sodium 2-(5-bromo-4-(4-cyclopropylnaphthalen-1-yl)-4H-1,2,4-triazol-3-ylthio)acetate, as described herein sufficient to inhibit the activity of URAT-1 in said mammal. In some embodiments, the invention provides methods of inhibiting URAT-1 activity in a human by contacting said human with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to inhibit the activity of URAT-1 in said human.

Pharmaceutical Compositions

Described herein are pharmaceutical compositions comprising an effective amount of a polymorphic, crystalline or mesophase form of sodium 2-(5-bromo-4-(4-cyclopropylnaphthalen-1-yl)-4H-1,2,4-triazol-3-ylthio)acetate, as described herein. In some embodiments, the pharmaceutical compositions comprise an effective amount of a polymorphic, crystalline or mesophase form of sodium 2-(5-bromo-4-(4-cyclopropylnaphthalen-1-yl)-4H-1,2,4-triazol-3-ylthio)acetate, as described herein, and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human. In some embodiments the pharmaceutical compositions are for the treatment or prophylaxis of disorders of uric acid metabolism. In some embodiments the pharmaceutical compositions are for the treatment or prophylaxis of hyperuricemia. In some embodiments the pharmaceutical compositions are for the treatment or prophylaxis of gout.

Modes of Administration, Formulations and Dosage Forms

Described herein are pharmaceutical compositions comprising a polymorphic, crystalline or mesophase form of sodium 2-(5-bromo-4-(4-cyclopropylnaphthalen-1-yl)-4H-1,2,4-triazol-3-ylthio)acetate, as described herein. The compound, compound forms and compositions described herein may be administered either alone or in combination with pharmaceutically acceptable carriers, excipients or diluents, in a pharmaceutical composition, according to standard pharmaceutical practice. Administration can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. Those of skill in the art will be familiar with administration techniques that can be employed with the compounds and methods of the invention. By way of example only, the compounds, compound forms and compositions described herein can be administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. The administration can also be by direct injection at the site of a diseased tissue or organ.

The pharmaceutical compositions described herein may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

The formulations may conveniently be presented in unit dosage form and may be prepared by any of the methods well known in the art of pharmacy. All methods include the step of bringing into association a compound or compound form of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Methods of preparing various pharmaceutical compositions with a specific amount of active compound are known, or will be apparent, to those skilled in this art.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. The pharmaceutical composition may be in unit dosage form. In such form, the preparation is subdivided into unit doses containing appropriate quantities of the active component, e.g., an effective amount to achieve the desired purpose. Determination of the proper dosage for a particular situation is within the skill of the art. For convenience, the total daily dosage may be divided and administered in portions during the day if desired. The amount and frequency of administration will be regulated according to the judgment of the attending clinician (physician) considering such factors as described above. Thus the amount of pharmaceutical composition to be administered may vary widely. When referring to a dosage amount, the quantity stated is of the active pharmaceutical ingredient. Administration may occur in an amount of between about 0.001 mg/kg of body weight to about 100 mg/kg of body weight per day (administered in single or divided doses), or at least about 0.1 mg/kg of body weight per day. A particular therapeutic dosage can include, e.g., from about 0.01 mg to about 7000 mg of compound, or, e.g., from about 0.05 mg to about 2500 mg. The quantity of active compound in a unit dose of preparation may be varied or adjusted from about 0.1 mg to 1000 mg, from about 1 mg to 300 mg, or 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. In combinational applications in which the compound is not the sole therapy, it may be possible to administer lesser amounts of compound and still have therapeutic or prophylactic effect.

Combination Therapies

The compounds and compound forms described herein may be administered as a sole therapy or in combination with another therapy or therapies.

By way of example only, if one of the side effects experienced by a patient upon receiving a compound or compound form as described herein is hypertension, then it may be appropriate to administer an anti-hypertensive agent in combination with the compound. Or, by way of example only, the therapeutic effectiveness of a compound or compound form as described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering a compound or compound form as described herein with another therapeutic agent (which also includes a therapeutic regimen) that also has therapeutic benefit. Regardless of the disease, disorder or condition being treated, the overall benefit experienced by the patient may simply be additive of the two therapeutic agents or the patient may experience a synergistic benefit.

In the instances where the compounds or compound forms as described herein are administered with other therapeutic agents, they need not be administered in the same pharmaceutical composition as other therapeutic agents, and may, because of different physical and chemical characteristics, be administered by a different route. For example, the compound or compound form as described herein may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The compounds, compound forms and compositions described herein (and where appropriate other chemotherapeutic agent) may be administered concurrently (e.g., simultaneously, essentially simultaneously or within the same treatment protocol) sequentially or separately, depending upon the nature of the disease, the condition of the patient, and the actual choice of other chemotherapeutic agent to be administered. For combinational applications and uses, the compounds, compound forms and compositions described herein and the chemotherapeutic agent need not be administered simultaneously or essentially simultaneously. Thus, the compounds, compound forms and compositions as described herein may be administered first followed by the administration of the chemotherapeutic agent; or the chemotherapeutic agent may be administered first followed by the administration of the compounds, compound forms and compositions as described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent may be administered first, especially if it is a cytotoxic agent, and then the treatment continued with the administration of the compounds, compound forms and compositions as described herein followed, where determined advantageous, by the administration of the chemotherapeutic agent, and so on until the treatment protocol is complete. Thus, in accordance with experience and knowledge, the practicing physician can modify each administration protocol for treatment according to the individual patient's needs, as the treatment proceeds. The attending clinician, in judging whether treatment is effective at the dosage administered, will consider the general well-being of the patient as well as more definite signs such as relief of disease-related symptoms. Relief of disease-related symptoms such as pain, and improvement in overall condition can also be used to help judge effectiveness of treatment.

Specific, non-limiting examples of possible combination therapies include use of the compounds and compositions described herein with Febuxostat, Allopurinol, Probenacid, Sulfinpyrazone, Losartan, Fenofibrate, Benzbromarone or PNP-inhibitors (such as, but not limited to Forodesine, BCX-1777 or BCX-4208). This list should not be construed to be closed, but should instead serve as an illustrative example common to the relevant therapeutic area at present. Moreover, combination regimens may include a variety of routes of administration, including but not limited to oral, intravenous, intraocular, subcutaneous, dermal, and inhaled topical.

Diseases

Described herein are methods of treating a disease or disorder in an individual suffering from said disease or disorder comprising administering to said individual an effective amount of a polymorph, crystalline form or mesophase as described herein of sodium 2-(5-bromo-4-(4-cyclopropyl-naphthalen-1-yl)-4H-1,2,4-triazol-3-ylthio)acetate.

The invention extends to the use of the compounds and compound forms described herein in the manufacture of a medicament for treating a disease or disorder.

In some embodiments, the disease or disorder is hyperuricemia. In certain instances, hyperuricemia is characterized by higher than normal blood levels of uric acid, sustained over long periods of time. In certain instances, increased blood urate levels may be due to enhanced uric acid production (~10-20%) and/or reduced renal excretion (~80-90%) of uric acid. In certain instances, causes of hyperuricemia may include obesity/weight gain, excessive alcohol use, excessive dietary purine intake (foods such as shellfish, fish roe, scallops, peas lentils, beans and red meat, particularly offal— brains, kidneys, tripe, liver), certain medications, including low-dose aspirin, diuretics, niacin, cyclosporine, pyrazinamide, ethambutol, some high blood pressure drugs and some cancer chemotherapeutics, immunosuppressive and cytotoxic agents, specific disease states, particularly those associated with a high cell turnover rate (such as malignancy, leukemia, lymphoma or psoriasis), and also including high blood pressure, hemoglobin diseases, hemolytic anemia, sickle cell anemia, various nephropathies, myeloproliferative and lymphoproliferative diseases, hyperparathyroidism, renal disease, conditions associated with insulin resistance and diabetes mellitus, and in transplant recipients, and possibly heart disease, inherited enzyme defects, abnormal kidney function (e.g. increased ATP turn over, reduced glomerular urate filtration) and exposure to lead (plumbism or "saturnine gout").

In certain instances, hyperuricemia may be asymptomatic, though is associated with the following conditions: gout, gouty arthritis, uric acid stones in the urinary tract (urolithiasis), deposits of uric acid in the soft tissue (tophi), deposits of uric acid in the kidneys (uric acid nephropathy), and impaired kidney function, possibly leading to chronic and acute renal failure.

In further or additional embodiments, the disease or disorder is gout, which is a condition that results from uric acid crystals depositing in tissues of the body. It is often related to an inherited abnormality in the body's ability to process uric acid, but may also be exacerbated by a diet high in purines. Defective uric acid processing may lead to elevated levels of uric acid in the blood causing recurring attacks of joint inflammation (arthritis), uric acid deposits in and around the joints, tophaceous gout, the formation of tophi, decreased kidney function, and kidney stones. Approximately 3-5 million people in the United States suffer from attacks of gout with attacks 6 to 9 times more common in men than in women (see Sanders and Wortmann, "Harrison's Principles of Internal Medicine", 16th Edition; 2005; Food and Drug Administration (FDA) Advisory Committee Meeting, Terkeltaub presentation, June 2004; Terkeltaub, "Gout", *N Engl J Med.*, 349, 1647-55, 2003). In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Gout is associated with hyperuricemia. In certain instances, individuals suffering from gout excrete approximately 40% less uric acid than nongouty individuals for any given plasma urate concentration. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining). Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels >9 mg/dL (530 µmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood diseases (e.g. polycythemia, myeloid metaplasia, etc).

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and last longer, especially if the disease is not controlled. In certain instances, episodes damage the affected joint(s) resulting in stiffness, swelling, limited motion and/or persistent mild to moderate pain.

Plumbism or "saturnine gout," is a lead-induced hyperuricemia that results from lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricaemia. In certain instances, saturnine gout is characterized by less frequent attacks than primary gout. In certain instances, lead-associated gout occurs in pre-menopausal women, an uncommon occurrence in non lead-associated gout.

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disease leads to severe gout, poor muscle control, and moderate mental retardation, which appear in the first year of life. In certain instances, the disease also results in self-mutilating behaviors (e.g., lip and finger biting, head banging) beginning in the second year of life. In certain instances, the disease also results in gout-like swelling in the joints and severe kidney problems. In certain instances, the disease leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of a compound described herein to an individual is useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels.

In some embodiments, a compound or compound form as described herein is administered to an individual suffering from a disease or condition requiring treatment with a diuretic. In some embodiments, a compound or compound form as described herein is administered to an individual suffering from a disease or condition requiring treatment with a diuretic, wherein the diuretic causes renal retention of urate. In some embodiments, the disease or condition is congestive heart failure or essential hypertension.

In some embodiments, administration of a compound or compound form as described herein to an individual is useful for improving motility or improving quality of life.

In some embodiments, administration of a compound or compound form as described herein to an individual is useful for treating or decreasing the side effects of cancer treatment.

In some embodiments, administration of a compound or compound form as described herein to an individual is useful for decreasing kidney toxicity of cis-platin.

In certain instances, gout is treated by lowering the production of uric acid. In certain instances, gout is treated by increasing the excretion of uric acid. In certain instances, gout is treated by URAT 1, xanthine oxidase, xanthine dehydrogenase, xanthine oxidoreductase, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i) reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the gout attack. In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, ice-packs, elevation and/or protection of the affected area/s. In certain instances, the aforementioned treatments do not prevent recurrent attacks and they do not affect the underlying diseases of abnormal uric acid metabolism.

ii) Preventing future attacks. In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

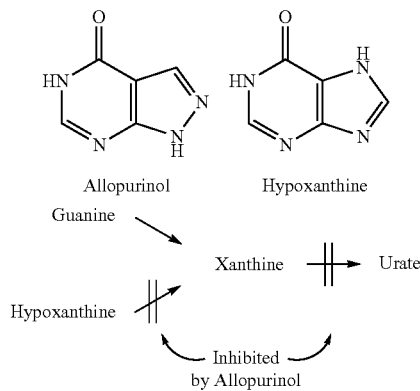

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for diseases of uric acid metabolism has not evolved significantly in the following two decades since the introduction of allopurinol.

In certain instances, uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels <6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Successful treatment aims to reduce both the pain associated with acute gout flare and long-term damage to the affected joints (Emerson, "The Management of Gout", N Engl J Med., 334(7), 445-451, 1996). Therapeutic goals include providing rapid and safe pain relief, preventing further attacks, preventing the formation of tophi and subsequent arthritis, and avoiding exacerbating other medical conditions. Initiation of treatment depends upon the underlying causes of hyperuricemia, such as renal function, diet, and medications. While gout is a treatable condition, there are limited treatments available for managing acute and chronic gout and a number of adverse effects are associated with current therapies. Medication treatment of gout includes pain management, prevention or decrease in joint inflammation during an acute gouty attack, and chronic long-term therapy to maintain decreased serum uric acid levels.

Nonsteroidal anti-inflammatory drugs (NSAIDs) are effective anti-inflammatory medications for acute gout but are frequently associated with irritation of the gastrointestinal (GI) system, ulceration of the stomach and intestines, and occasionally intestinal bleeding (Schlesinger, "Management of Acute and Chronic Gouty Arthritis Present State-of-the-Art"; *Medications;* 64 (21), 2399-2416, 2004; Pascual and Sivera, "Therapeutic advances in gout"; *Curr Opin Rheumatol.*, March; 19(2), 122-7, 2007). Colchicine for acute gout is most commonly administered orally as tablets (every 1-2 hours until there is significant improvement in pain or the patient develops GI side effects such as severe diarrhea, nausea and vomiting), or intravenously. Corticosteroids, given in short courses, can be administered orally or injected directly into the inflamed joint.

Medications are available for reducing blood uric acid levels that either increase renal excretion of uric acid by inhibiting re-uptake or reduce production of uric acid by blockade of xanthine oxidase. These medicines are generally not initiated until after the inflammation from acute gouty arthritis has subsided because they may intensify the attack. If they are already being taken prior to the attack, they are continued and only adjusted after the attack has resolved. Since many subjects with elevated blood uric acid levels may not develop gouty attacks or kidney stones, the decision for prolonged treatment with uric acid-lowering medications is individualized.

Kits

The compounds, compound forms, compositions and methods described herein provide kits for the treatment of diseases and disorders, such as the ones described herein. These kits comprise a compound, compound form, compounds, compound forms or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The compounds, compound forms and pharmaceutical compositions described herein may be utilized for diagnostics and as research reagents. For example, the compounds, compound forms and pharmaceutical compositions, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds, compound forms and pharmaceutical compositions described herein are also useful for veterinary treatment of companion animals (e.g. dogs, cats), exotic animals and farm animals (e.g. horses), including mammals, rodents, and the like.

The examples and preparations provided below further illustrate and exemplify the compounds of the present invention and methods of preparing such compounds. It is to be understood that the scope of the present invention is not limited in any way by the scope of the following examples and preparations.

EXAMPLES

Lesinurad

Lesinurad is the generic name for 2-(5-bromo-4-(4-cyclopropylnaphthalen-1-yl)-4H-1,2,4-triazol-3-ylthio)acetic acid, whose chemical structure is:

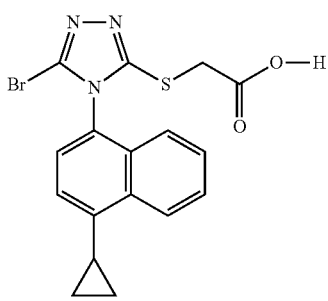

In some instances, the term Lesinurad also includes the sodium salt of Lesinurad, i.e. sodium 2-(5-bromo-4-(4-cyclopropylnaphthalen-1-yl)-4H-1,2,4-triazol-3-ylthio)acetate. In the examples described herein, the compound administered may be Lesinurad, or its sodium salt, in an amorphous or polymorph form thereof. In instances where the sodium salt is used, the amounts quoted herein may in fact be lower than the actual amounts of the sodium salt of Lesinurad used in the experiment, but were calculated to provide an effective amount of the free acid compound.

I. In Vitro Experiments

Example 1

Comparison of Lesinurad to Other Gout Therapies

Figure 2:
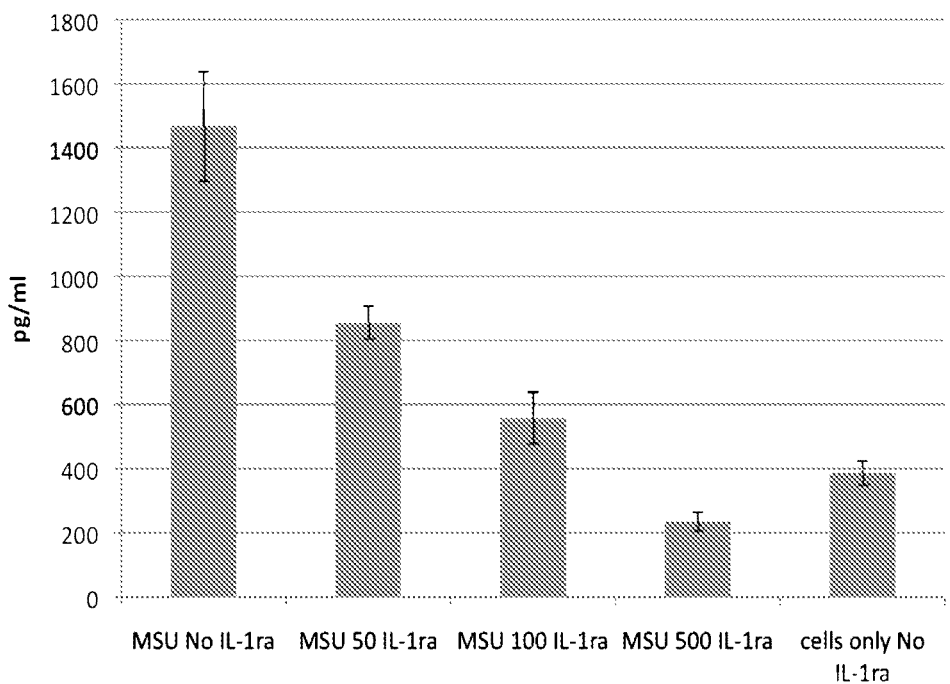
FIG. 2 illustrates the effect of rilonacept (IL-1ra) on TNF-α (FIG. 2A) and IL-1β production (FIG. 2B).
Figure 2:
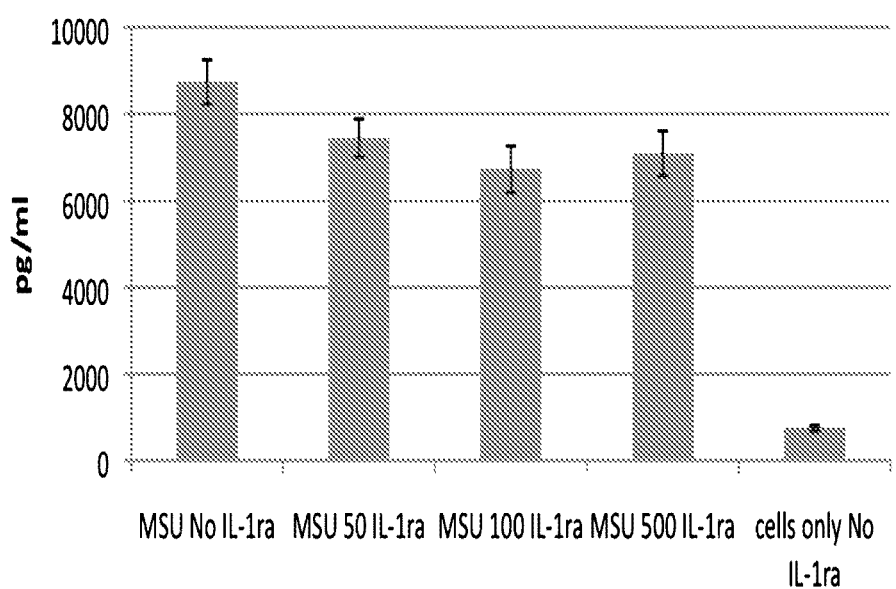

Activation of the inflammasome results in the release of preformed IL-1, which goes on to activate other targets as well as increase the production of IL-1 itself. Lesinurad blocks IL-1 release very early, within 1 hour of stimulation, as illustrated in FIG. 1. This activity may be compared with rilonacept which only inhibits the production of TNF-α, (as expected since TNF-α production is downstream of IL-1β action) as illustrated in FIG. 2A (6 hour time point). However, rilonacept does not reduce IL-1 production as illustrated in FIG. 2B.

Example 2

In Vitro MSU-Induced Inflammation to Assess the Effect of Lesinurad on Human Cells Example 2A In Vitro THP-1 (Human Cell) Assay STEP A: Preparation of MSU Crystals Uric acid (2 g, Sigma, Cat #U0881, Log S89329-419) was heated in a flask at 200° C. for 2 hours. Endotoxin free water (396 mL) followed by aqueous sodium hydroxide solution (2.375 mL of 5N or 1.19 mL 10N) were added and heated on a stir plate until the uric acid dissolved. It was then cooled, filtered (stericup filter), and the pH measured (pH 7.9). The solution was stirred at room temperature for 24 hours and then centrifuged at 1000 g for 10 min. The supernatant was discarded and resuspended in PBS and centrifuged at 1000 g for 10 min; this step was repeated twice. The washed crystals were heated at 60° C. until dry and then autoclaved at 200° C. for 2 hours. The crystals were then weighed and resuspended in PBS at a concentration of 26 mg/ml.

STEP B: Assay Details

THP-1 cells were differentiated with 0.5 μM of phorbol myristate acetate (PMA) incubated for 3 hours. Cells were then spun down and washed once with HBSS. $1.25 \times 10^6$/mL cells were plated in white clear bottom white 96 well plate in 100 μL volume and incubated overnight. The next day the media was aspirated from the wells. 100 μL of 1× Optimem along with the compounds were added. The cells and Lesinurad were incubated at 37° C. for 6 hours. 75 ul of the supernatant was collected and frozen to −20° C. for cytokine/chemokine analysis by MSD. 10 μL of CellTiter-Glo (Promega) was added to the assay plate and incubated at R.T for 15 mins and then read on analyst.

STEP C: IL-1β and TNF-α

Figure 3:
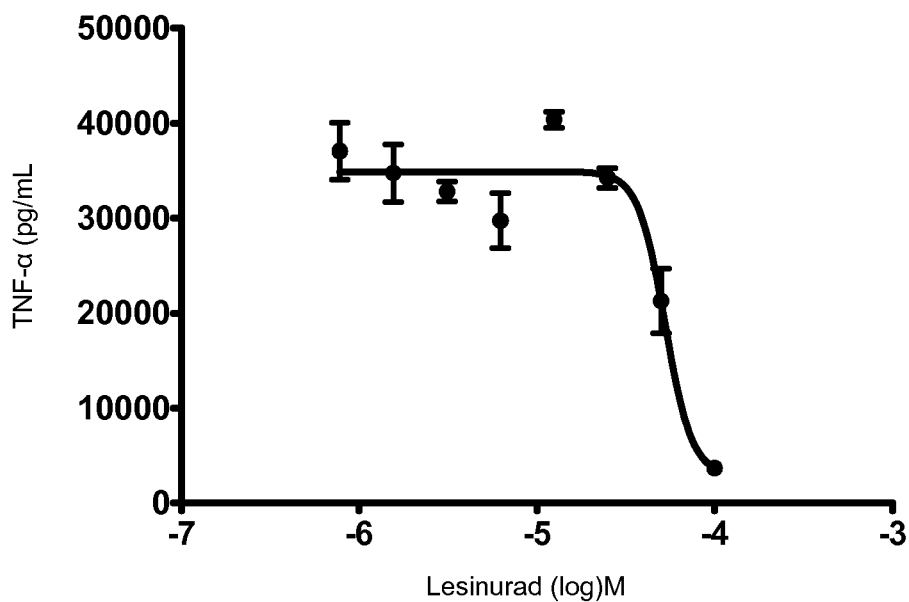
FIG. 3 illustrates the effect of Lesinurad on TNF-α (FIG. 3A) and IL-1β (FIG. 3B) production in differentiated THP-1 cells
Figure 3:
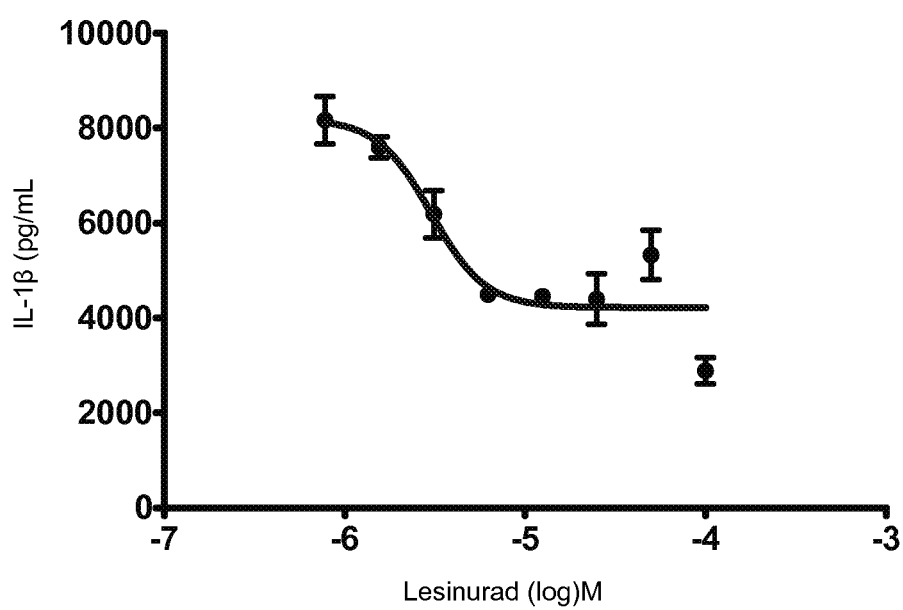

FIG. 3A shows a plot of Lesinurad concentration (log) versus TNF-α concentration (pg/ml), generating a Lesinurad TNF-α $IC_{50}$~52 uM. FIG. 3B shows a plot of Lesinurad concentration (log) versus IL-1β concentration (pg/ml), generating a Lesinurad IL-1β $IC_{50}$~30 uM.

Example 2B

In Vitro Primary Human Monocyte Assay

STEP A: Isolation of human Peripheral Blood Mononuclear Cells (hPBMCs)

Blood (50-60 ml) was collected in Heparin vaccutainers (BD vaccutainer, Cat No-367874, Sodium Heparin, 10 ml tube; each holding ~8-10 ml blood), which was immediately mixed to prevent coagulation. Accuspin-Histopaque 1077 (Sigma Aldrich cat no-A7054) was allowed to reach room temperature and diluted blood 1:1 in DPBS (Dulbecco's Phosphate-Buffered Saline (1×), liquid—Invitrogen, 14040-133), mixed by pipetting. The tubes were centrifuged (800 g; 30 seconds; room temp) to ensure all the Histopaque 1077 was below the high density polyethylene barrier.

Diluted blood (50 ml) was added to the upper chamber of each ACCUSPIN tube and centrifuged at room temp for 10 minutes at 1000×g or 15 minutes at 800×g, (brakes were off for this step; acc=1, dcl=1). PBMCs were collected from the PBS/Ficoll interphase with a transfer pipette and transferred to a new 50 mL tube. 10% RPMI was added to bring the volume to 40 ml and the cells spun down at 240×g (1000 rpm), 8 min at room temp.

Supernatant was decanted and 5 mL of RBC lysis solution added to the pellet and mixed well. The tubes were incubated at room temp for 5 mins, diluted to 10 mL with DPBS and spun down at 240×g (1000 rpm), 8 min, room temp. The supernatant was discarded, resuspended in RPMI complete media, and the cells counted.

Materials and Reagents:
RBC lysis buffer—Miltenyi Biotec Red Blood Cell Lysis Solution (#130-094-183)
RPMI—RPMI Medium 1640 (1×), liquid Cat. No. 11875-135
FBS—Fetal Bovine Serum, Qualified, Heat-Inactivated Cat. No. 16140-071
10% RPMI—RPMI+10% FBS
DMSO—Opti-Freeze DMSO Cryopreservation Medium, Fisher BioReagents, Cat NO BP2652-50
Freezing media—50% FBS+40% RPMI+10% DMSO STEP B: Isolation of Monocytes The hPBM cells isolated in step A were counted, centrifuged (300 g; 10 min) and the supernatant aspirated. The cell pellet was resuspended in 80 ul of buffer per 10^7 total cells, and 20 ul of CD14 Microbeads per 10^7 cells added and after mixing incubated on ice 15 mins. The cells were washed by adding 5 ml of MACs buffer and centrifuged (300 g; 10 mins).

While the cells were being centrifuged, the MACS MS column was equilibrated by placing the column onto the magnet. 15 ml conical tube was placed below the column to collect the flow through. 3 ml of MACS buffer was added to the column to equilibrate it; flow through was discarded and a new 15 ml tube placed under the column.

The centrifuged cells were then resuspended in 5 ml of MACS buffer and applied to the column. The flow through was discarded. The column was then removed from the magnet and placed on a new 15 ml tube. 3 ml of MACS buffer was added to the column and the flow through containing the monocytes collected. Cells were spun down (300 g, 5 min; supernatant discarded), resuspended in RPMI complete media and counted.

Materials and Reagents:
Miltenyi Bio's Monocyte Isolation kit II—Cat No—130-050-201
MACS buffer: PBS—pH 7.2 100 ml; 0.5% FBS; 2 mM EDTA
RPMI complete media recipe: 10% heat inactivated fetal bovine serum
RPMI 1640: 1% PenStrepGlut; 1% Non-Essential Amino Acid; 1% Hepes; 1% Na-pyruvate; BME
GPCR study performed by Life Technologies
Chemotaxis assay performed by Bio-quant (in primary human monocytes, neutrophils and T cells).

STEP C: IL-1β and CLU

Figure 4:
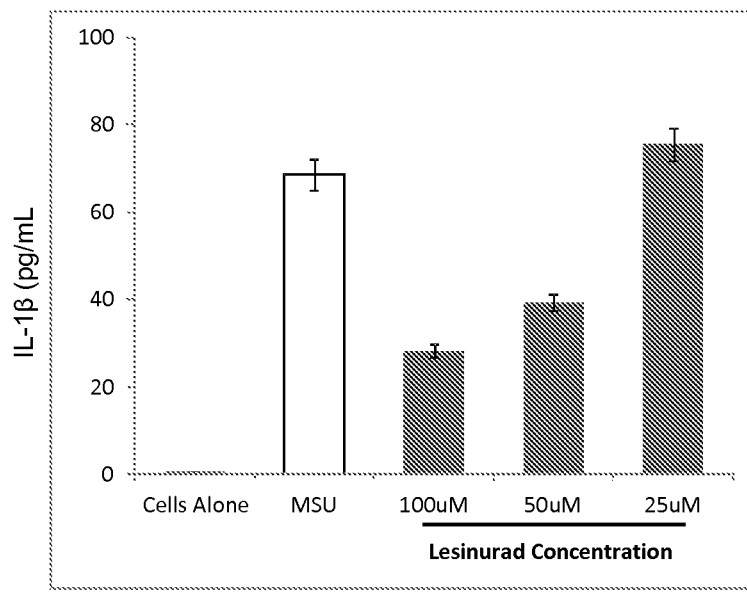
FIG. 4 illustrates the effect of Lesinurad on IL-1β (FIG. 4A) and the CLU count in a CellTiter-Glo® assay (FIG. 4B).
Figure 4:
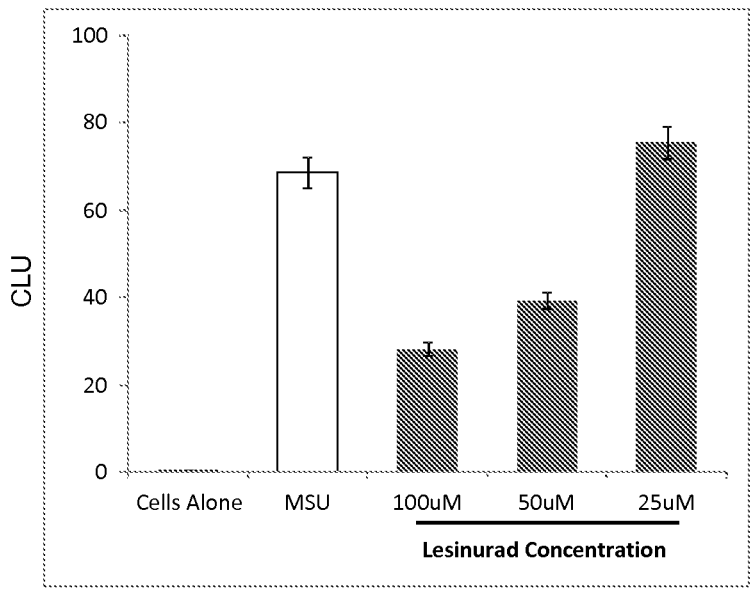

FIG. 4A shows a plot of IL-1β (pg/ml) for varying concentrations of Lesinurad (100 uM, 50 uM and 25 uM), indicating dose dependent IL-1β inhibition with a Lesinurad an IL-1β $IC_{50}$~50 uM. FIG. 4B shows a plot of CLU for varying concentrations of Lesinurad (100 uM, 50 uM and 25 uM).

II In Vivo Rat Studies

Example 3

Effect of Orally Administered Lesinurad on Monosodium Urate (MSU) Crystal-Induced Inflammation in Rats Example 3A Effects of Lesinurad in a Rat Air Pouch Model of Crystal-Induced Arthropathy Procedure
1. Preparation of monosodium urate (MSU) crystals.
   a. 1.68 g uric acid was dissolved in 500 ml 0.01 NaOH and heated to 70° C. NaOH was added as required to maintain pH 8-9. The solution was filtered and incubated at ambient with slow stirring continuously for 24 hours.
   b. Crystals were washed, dried and sterilized by autoclaving.
   c. Crystals were suspended in sterile saline at 0.67 mg/ml, 2.67 mg/ml and 10 mg/ml just prior to use.
2. 110 Sprague-Dawley rats (male, 160-180 g) were quarantined for 3 days; rats were accepted for the Study if no signs of clinical distress were noted during the quarantine period. The rats were maintained on certified laboratory diet and water ad libitum.
3. The rats were ear-notched for individual identification and rat weights were recorded.
4. The rats were distributed randomly to 11 groups of 10 rats per group based upon average weight.
5. The rats were anesthetized and bled for sample from retro-orbital sinus into microtainer tubes.
   a. The blood was processed to serum;
   b. The serum was transferred to labeled Eppendorf tubes (T=0) and stored at −80° C.
   c. Minimum serum volume of 100 μl (or 200 μl blood) was collected from each rat.
6. DAY 0: The rats are anesthetized.
   a. The nape of the neck was shaved, cleansed with 70% isopropanol followed by cleansing with Povidone.
   b. A 23-gauge needle was attached to a 30 ml syringe fitted with an air filter.
   c. 30 ml of sterile air was injected subcutaneously and the rat returned to routine maintenance.
7. DAY 3: Steps 6a) through 6c) were repeated.
8. DAYS 4 and 5:
   a. Rats in test compound groups were dosed once daily by subcutaneous injection or oral dosing as in the treatment table below.
   b. 24 hours after dosing on DAY 4 (DAY 5), sample bleeds are collected from each rat immediately prior to dosing on DAY 5, processed to serum and stored at −80° C. A minimum of 0.100 ml serum was collected for each bleed.
9. DAY 6: TIME=0 HOUR: Rats were injected subcutaneously with Colchicine or dosed orally with Vehicle, Lesinurad or Allopurinol.
   Lesinurad formulation: Lesinurad was dissolved in distilled water ($dH_2O$) to prepare a 20 mg/ml dosing solution (Group 10). The 20 mg/ml stock was diluted in $dH_2O$ to prepare a 6 mg/ml solution (Group 9) and a 2 mg/ml solution (Group 8).
   Allopurinol formulation: Allopurinol was dissolved in distilled water ($dH_2O$) to prepare a 2 mg/ml dosing solution (Group 11).
   Immediately following SC injections, each animal was injected intravenously with Evans blue dye (2.5% w/vol; 2.0 ml/kg). Evans blue binds to albumin and acts as a marker for plasma extravasation.
10. Group Treatments are shown in Table 1.

TABLE 1

Group Treatment Schedule

| Group | No. Rats | Treatment | Dose (mg/kg) | ROA | Timing | MSU (mg) |
|---|---|---|---|---|---|---|
| 1 | 10 | Vehicle | N/A | PO | −30 min | None |
| 2 | 10 | Vehicle | N/A | PO | −30 min | 10 |
| 3 | 10 | Vehicle | N/A | PO | −30 min | 40 |
| 4 | 10 | Vehicle | N/A | PO | −30 min | 150 |
| 5 | 10 | Colchicine | 0.01 | SC | −30 min | 150 |
| 6 | 10 | Colchicine | 0.1 | SC | −30 min | 150 |
| 7 | 10 | Colchicine | 1 | SC | −30 min | 150 |
| 8 | 10 | Lesinurad | 10 | PO | −30 min | 150 |
| 9 | 10 | Lesinurad | 30 | PO | −30 min | 150 |
| 10 | 10 | Lesinurad | 100 | PO | −30 min | 150 |
| 11 | 10 | Allopurinol | 10 | PO | −30 min | 150 |

11. Thirty minutes after treatment, the rats were anesthetized and injected into the air pouch with 15 ml MSU suspension.

12. Four (4) hours after MSU injection, the rats were anesthetized and bled for sample from retro-orbital sinus into microtainer tubes.
   a. The blood was processed to serum
   b. The serum was transferred to labeled Eppendorf tubes (T=0) and stored at −80° C.
   c. Minimum serum volume of 100 µl (or 200 µl blood) was collected from each rat.
   d. 5 ml sterile PBS containing 10 U/ml heparin injected into the air pouch of anesthetized rats.
13. The pouch was gently massaged and the exudate was immediately removed from the air pouch. Exudates volume was measured and recorded for each animal.
   a. Exudate cells were collected by centrifugation at 2,000 rpm for 5 minutes at room temperature. The supernatants were aliquoted to two portions and stored at −80° C.
   b. Cells were re-suspended in 0.5 ml heparinized saline for neutrophil cell counts.
   c. Plasma extravasation was measured by optical absorbance at 620 nm for each exudate sample.
14. Exudate from each animal was assayed for TNF-alpha and IL-1.
15. Data treatments:
   a. Mean cell counts and standard deviations were determined for each group.
   b. Mean optical absorbance measurements and standard deviations were determined for each group.
   c. Group means and standard deviations for TNF-alpha and IL-1 were determined for each group.
   d. Statistical significance of treatments on mean cell counts, mean optical absorbance measurements and mean cytokine measurements were determined by comparison of means for treatment and positive control groups with vehicle group.

Results

Figure 5:
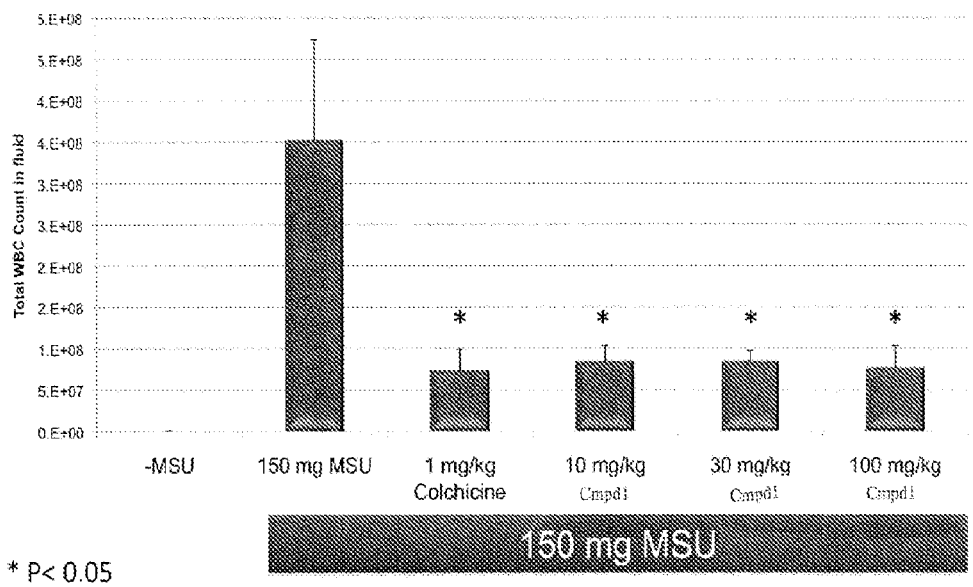
FIG. 5 illustrates the effect of Lesinurad (Comp1) in a rat model of inflammation in comparison with 1 mg/kg colchicine (FIG. 5A) and 0.1 mg/kg colchicine (FIG. 5B).
Figure 5:
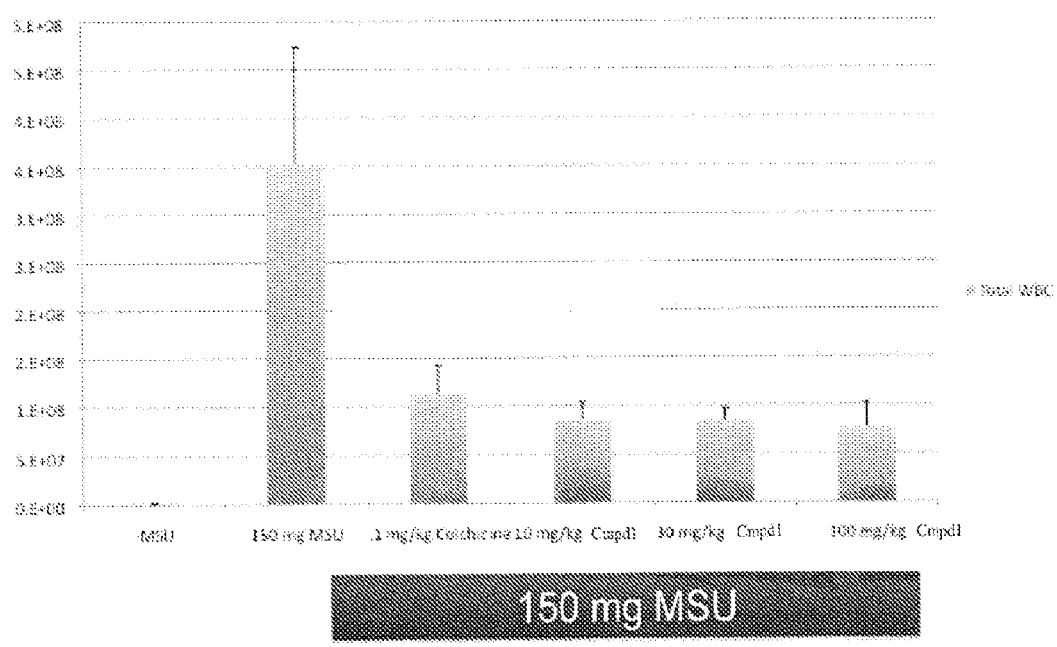

As shown in FIG. 5, (total white blood cell counts for 10 mg/kg, 30 mg/kg and 100 mg/kg Lesinurad) monosodium urate crystal-induced inflammatory response was blocked by Lesinurad. FIG. 5A provides the comparison with 1 mg/kg colchicine. FIG. 5B provides the comparison with 0.1 mg/kg colchicine.

Example 3B

In Vivo MSU-Induced Inflammation—Rat Air Pouch Study

The objective of this study was to assess the effect of Lesinurad (dosed orally, 0.1-60 mg/kg QD) in monosodium urate (MSU) crystal injection-induced inflammation in rats.

STEP A: Animals and Animal Care

Male Sprague-Dawley rats weighing 130-200 g from Harlan, Indianapolis, Ind. (Air Pouch studies) were unpacked, placed in cages, a health inspection performed and a number assigned. Rats were caged in groups of 3-5 with free access to certified laboratory rodent chow and drinking water, in environmentally-controlled rooms (20-26° C.; 40-70% relative humidity), with time-controlled fluorescent lighting systems providing 12/12 dark light cycle.

STEP B: Method

Under anesthesia, 30 mL sterile air was injected subcutaneously on day 0 and day 3. Vehicle (water) or Lesinurad were administered orally. On the day of the experiment, rats were dosed with Vehicle, Lesinurad p.o., and/or colchicine s.c. (Sigma, Cat.#C9754, Lot.#188K1131). Immediately following administrations, each animal was injected i.v. with Evans blue dye (2.5% w/vol; 2.0 ml/kg), which binds to albumin and acts as a plasma extravasation marker. 30 min post drug administration, the rats were anesthetized and the air pouch injected with 15 ml of either saline or MSU suspension (10 mg/mL). Four (4) hours after MSU injection, 5 ml of sterile PBS containing 10 U/ml heparin was injected into the air pouch of anesthetized rats. The pouch was gently massaged and the exudate was immediately removed from the air pouch. The exudate volume was measured and recorded for each animal. Cells in the exudate were collected by centrifugation (2,000 rpm; 5 mins; rt). The supernatants were stored at −20° C. for cytokine analysis. Cells were re-suspended in 0.5 ml heparinized saline for neutrophil cell counts. Plasma extravasation was measured by optical absorbance at 620 nm for each exudate sample. Blood sample bleeds were collected from each animal to provide 0.5 ml minimum volume of serum per rat.

STEP C: Extravasation (Optical Absorbance at 620 nm)

Figure 6:
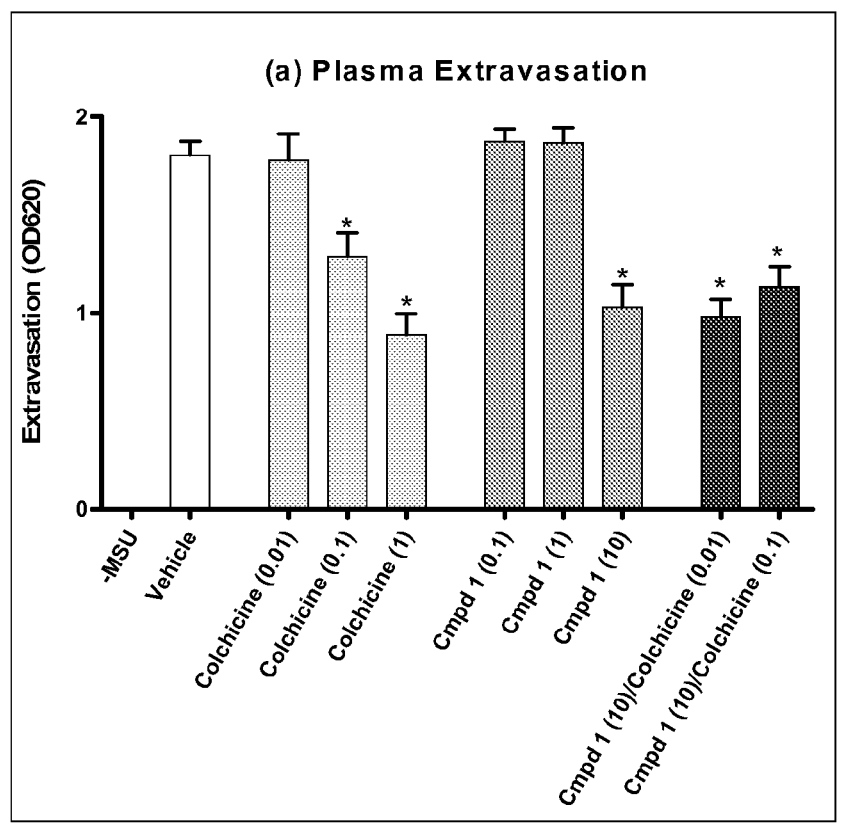
FIG. 6 illustrates in vivo MSU-induced inflammation in a rat air pouch study for various doses of Lesinurad p.o. (0.1, 1, 10 mg/kg/day), colchicine s.c. (0.01, 0.1, 1 mg/kg), and Lesinurad and colchicine (* indicates p<0.05 versus vehicle).
Figure 6:
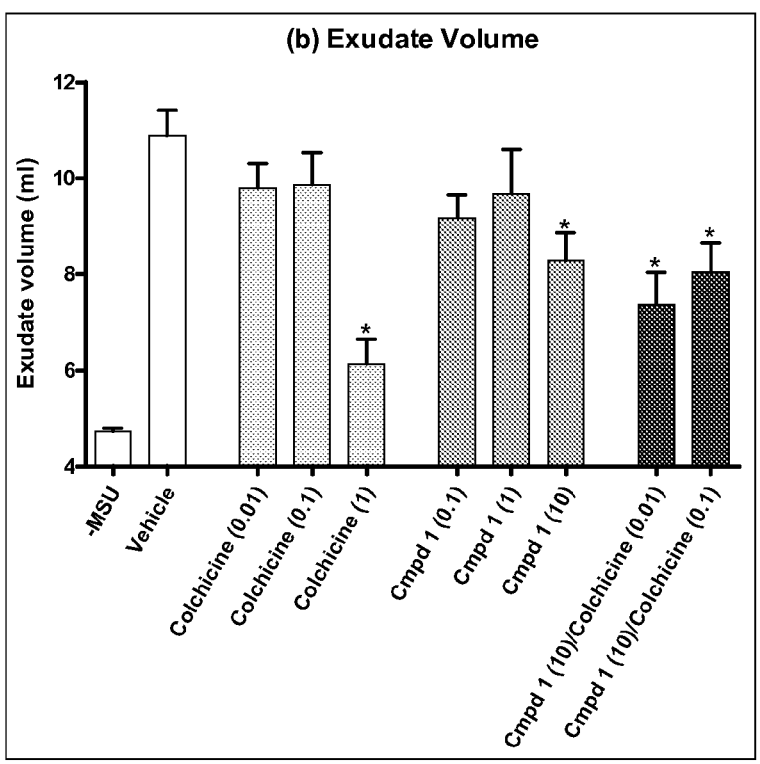
Figure 6:
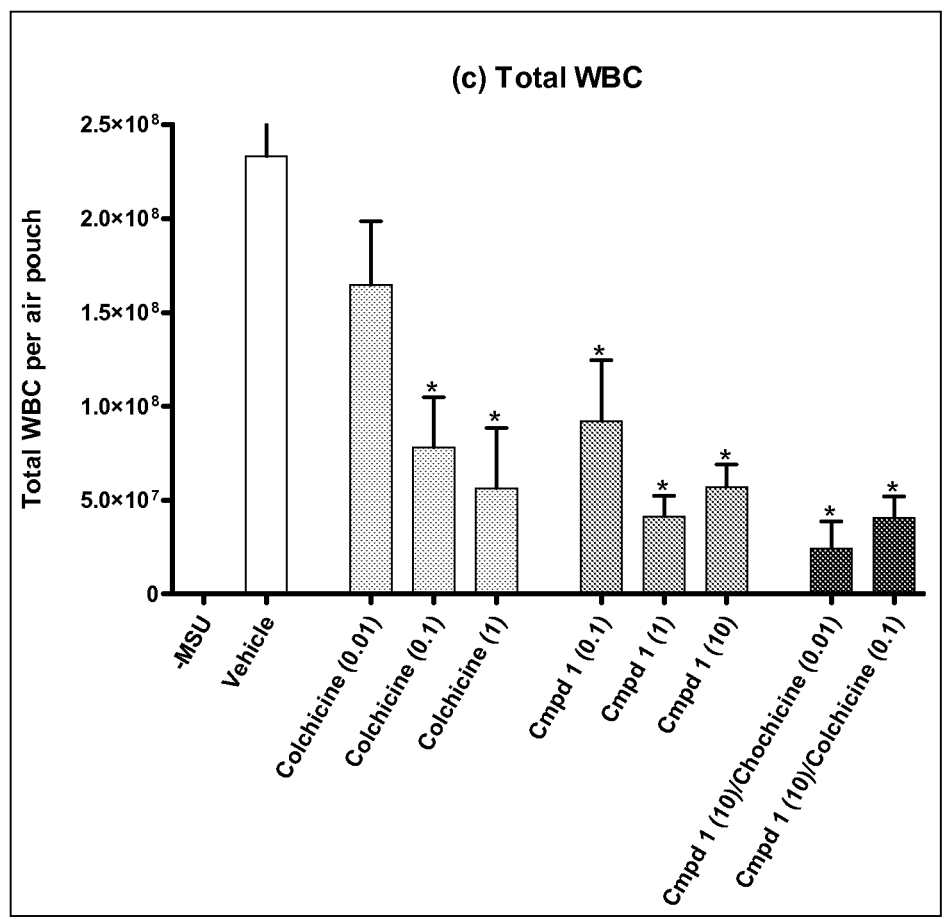

Extravasation values for various doses of Lesinurad and/or colchicine are shown in Table 2 below and in FIG. 6A, demonstrating:

Saline injection (no MSU) produces no detectable extravasation;

MSU crystal injection induces extravasation;

Colchicine (0.01, 0.1 and 1 mg/kg) showed a dose-dependent decrease in extravasation;

Lesinurad (10 mg/kg) reduced extravasation.

TABLE 2

Extravasation Values for Various Doses of Lesinurad and/or Colchicine

| Regimen | Dose mg/kg | 1 | 2 | 3 | 4 | 5 | 6 | 7 | 8 | 9 | 10 | Av |
|---|---|---|---|---|---|---|---|---|---|---|---|---|
| [1]Control | — | 0.00 | −0.01 | 0.00 | 0.00 | −0.01 | −0.01 | −0.02 | −0.01 | 0.00 | −0.01 | −0.01 |
| [2]Vehicle | — | 2.16 | 1.42 | 1.68 | 1.94 | 1.66 | 1.80 | 1.76 | 1.89 | 2.11 | 1.62 | 1.80 |
| Colchicine | 0.01 | 1.46 | 1.67 | 1.63 | 1.74 | 2.62 | 2.39 | 1.99 | 1.42 | 1.34 | 1.53 | 1.78 |
|  | 0.1 | 1.31 | 1.74 | 0.68 | 1.75 | 1.72 | 0.98 | 0.83 | 1.22 | 1.25 | 1.41 | 1.29 |
|  | 1 | 1.17 | 1.19 | 1.24 | 1.24 | 1.12 | 0.52 | 0.73 | 0.59 | 0.75 | 0.36 | 0.89 |
| Lesinurad | 0.1 | 1.89 | 2.19 | 1.54 | 2.14 | 1.94 | 1.61 | 1.90 | 1.88 | 1.84 | 1.83 | 1.87 |
|  | 1 | 2.27 | 1.36 | 1.94 | 1.67 | 1.79 | 1.98 | 2.04 | 1.83 | 1.79 | 2.01 | 1.87 |
|  | 10 | 0.89 | 0.77 | 0.71 | 0.97 | 0.82 | 1.94 | 0.82 | 1.25 | 1.20 | 0.93 | 1.03 |
| Lesinurad/ Colchicine | 10/0.01 | 0.71 | 1.24 | 1.04 | 1.08 | 0.78 | 0.70 | 1.23 | 0.70 | 0.84 | 1.51 | 0.98 |
|  | 10/0.1 | 0.82 | 1.06 | 1.07 | 1.11 | 1.21 | 1.36 | 1.31 | 1.35 | 1.63 | 0.43 | 1.13 |

[1]Control = no MSU;
[2]Vehicle = sterile saline

STEP D: Exudate Volume

Exudate volume values (mL) for various doses of Lesinurad and/or colchicine are shown in Table 3 below and in FIG. 6B, demonstrating:

- In vehicle-treated rats, the amount of exudate more than doubles
- At 0.01 and 0.1 mg/kg doses colchicine did not significantly reduce exudate volume.
- At 1 mg/kg colchicine significantly reduced exudate volume.
- At 0.1 and 1 mg/kg/day doses Lesinurad 1 did not significantly reduce exudate volume.
- At 10 mg/kg/day Lesinurad significantly reduced exudate volume.
- Lesinurad 10 mg/kg/day co-administered with colchicine (0.01 and 0.1 mg/kg), did not significantly reduce exudate volume better than either therapy alone.
- A number of cytokines in the exudates were measured; Lesinurad significantly reduced IL-4 levels.

TABLE 3

Exudate Volume Values for Various Doses of Lesinurad and/or Colchicine

| Regimen | Dose mg/kg | 1 | 2 | 3 | 4 | 5 | 6 | 7 | 8 | 9 | 10 | Av |
|---|---|---|---|---|---|---|---|---|---|---|---|---|
| Control | | 4.6 | 4.6 | 5 | 4.9 | 5 | 4.2 | 4.6 | 4.9 | 4.8 | 4.6 | 4.72 |
| Vehicle | | 12 | 9 | 14 | 10.8 | 10 | 12 | 11 | 10 | 12 | 8 | 10.88 |
| Colchicine | 0.01 | 10 | 9 | 9 | 12 | 8 | 11 | 11 | 8 | 12 | 8 | 9.8 |
| | 0.1 | 10 | 7.8 | 8 | 9.8 | 11 | 11 | 15 | 9 | 9 | 8 | 9.86 |
| | 1 | 7 | 5.9 | 8 | 8.6 | 5.6 | 4.6 | 4 | 5.2 | 8 | 4.4 | 6.13 |
| Lesinurad | 0.1 | 11 | 8 | 10 | 9.6 | 9.2 | 7 | 8 | 12 | 8 | 9 | 9.18 |
| | 1 | 13 | 5 | 10 | 12 | 14 | 7.8 | 11.4 | 7 | 9.6 | 7 | 9.68 |
| | 10 | 6 | 8 | 6 | 9 | 12 | 8.4 | 9 | 7.5 | 7 | 10 | 8.29 |
| Lesinurad/ | 10/0.01 | 11 | 9 | 8 | 9 | 5 | 5 | 7 | 4.9 | 6 | 8.8 | 7.37 |
| Colchicine | 10/0.1 | 7.8 | 8 | 5 | 8 | 10 | 7 | 11 | 9 | 9.6 | 5 | 8.04 |

[1]Control = no MSU;
[2]Vehicle = sterile saline

STEP E: White Blood Cell (WBC) Count

Total numbers of white blood cells are shown in the table below ($\times 10^8$) for various doses of Lesinurad and/or colchicine are shown in Table 4 and graphically in FIG. 6C, demonstrating:

- Four hours after MSU injection, there are significant amounts of white blood cells in the air pouch;
- Colchicine dose-dependently lowered the number of white blood cells;
- Lesinurad (0.1, 1 and 10 mg/kg/day) significantly lowered the number of white blood cells;
- Lesinurad (10 mg/kg/day) co-administered with colchicine (0.01 or 0.1 mg/kg), did not significantly reduce the number of white blood cells better than either therapy alone.

TABLE 4

White Blood Cell Count for Various Doses of Lesinurad and/or Colchicine

| Regimen | Dose mg/kg | 1 | 2 | 3 | 4 | 5 | 6 | 7 | 8 | 9 | 10 | Av |
|---|---|---|---|---|---|---|---|---|---|---|---|---|
| Control | | 0.00 | 0.00 | 0.00 | 0.00 | 0.00 | 0.00 | 0.00 | 0.00 | 0.01 | 0.00 | 0.00 |
| Vehicle | | 1.98 | 1.49 | 5.88 | 3.02 | 4.05 | 3.24 | 0.74 | 0.33 | 0.18 | 2.40 | 2.33 |
| Colchicine | 0.01 | 3.40 | 0.63 | 2.27 | 0.90 | 2.22 | 2.42 | 0.69 | 0.34 | 0.87 | 2.72 | 1.65 |
| | 0.1 | 2.60 | 1.21 | 0.32 | 1.27 | 1.51 | 0.03 | 0.06 | 0.27 | 0.41 | 0.14 | 0.78 |
| | 1 | 3.43 | 0.32 | 0.52 | 0.26 | 0.35 | 0.03 | 0.09 | 0.26 | 0.36 | 0.01 | 0.56 |
| Lesinurad | 0.1 | 0.14 | 2.28 | 2.75 | 0.48 | 0.92 | 0.03 | 2.00 | 0.39 | 0.14 | 0.07 | 0.92 |
| | 1 | 0.68 | 0.01 | 0.48 | 0.54 | 0.26 | 1.17 | 0.34 | 0.02 | 0.19 | 0.44 | 0.41 |
| | 10 | 0.08 | 0.16 | 0.55 | 1.01 | 1.02 | 0.95 | 0.29 | 0.90 | 0.60 | 0.15 | 0.57 |
| Lesinurad/ | 10/0.01 | 0.06 | 0.03 | 0.08 | 1.53 | 0.09 | 0.05 | 0.02 | 0.25 | 0.20 | 0.13 | 0.24 |
| Colchicine | 10/0.1 | 0.21 | 1.24 | 0.18 | 0.50 | 0.65 | 0.35 | 0.41 | 0.47 | 0.03 | 0.04 | 0.41 |

Example 3C

In Vivo MSU-Induced Inflammation—Rat Knee Joint Study

The objective of this study was to assess the effect of Lesinurad (dosed orally, 0.1-60 mg/kg QD) in monosodium urate (MSU) crystal injection-induced inflammation in rats.

STEP A: Animals and Animal Care

Male Sprague-Dawley rats weighing 130-200 g from Shanghai SLAC Laboratory Animal Co., Ltd., China were unpacked, placed in cages, a health inspection performed and a number assigned. Rats were caged in groups of 3-5 with free access to certified laboratory rodent chow and drinking water, in environmentally-controlled rooms (20-26° C.; 40-70% relative humidity), with time-controlled fluorescent lighting systems providing 12/12 dark light cycle.

STEP B: Method

Rats were randomized into 7 groups on the basis of body weight on Day 1 and treated according to the Table 5 below.

TABLE 5

Group Treatment Schedule

| Gp | n | Treatment | Dose mL/kg | Dose mg/kg | Route | Dose/Day | Knee joint injection |
|---|---|---|---|---|---|---|---|
| 1 | 10 | ¹Vehicle | 10 | — | p.o. | Day1-Day7 (Once daily) | Saline |
| 2 | 15 | ¹Vehicle | 10 | — | p.o. | Day1-Day7 (Once daily) | ²MSU |
| 3 | 10 | Colchicine | 1 | 0.1 | p.o. (¹Vehicle); s.c. (Colchicine) | Day1-Day6 (¹Vehicle); Day7 (Colchicine) | ²MSU |
| 4 | 10 | Colchicine | 1 | 0.3 | p.o. (¹Vehicle); s.c. (Colchicine) | Day1-Day6 (¹Vehicle); Day7 (Colchicine) | ²MSU |
| 5 | 15 | Colchicine | 1 | 1 | p.o. (Vehicle); s.c.(Colchicine) | Day1-Day6 (¹Vehicle); Day7 (Colchicine) | ²MSU |
| 6 | 15 | Lesinurad | 10 | 60 | p.o. | Day1-Day7 (Once daily) | ²MSU |
| 7 | 10 | Lesinurad & Colchicine (0.1 mg/kg) | 10 | 60 | p.o. (Lesinurad); s.c.(Colchicine) | Day1-Day7 (Lesinurad); Day7(Colchicine) | ²MSU |

¹Vehicle = sterile water;
²MSU = monosodium urate

Groups 1 and 2 were orally dosed with Vehicle (sterile water) once daily for seven days from Day 1. Groups 3, 4 and 5 were orally dosed with Vehicle from Day 1 to Day 6, on Day 7 they received colchicine administered subcutaneously. Groups 6 and 7 were orally dosed with Lesinurad once daily for seven days from Day 1; Group 7 also received colchicine administered subcutaneously on Day 7.

Thirty minutes post dosing on Day 7, rats were anesthetized and the diameter and surface temperature of right knee joints were measured. Sterilized MSU crystals (6 mg) suspended in sterile saline (0.05 mL) were injected into a knee joint cavity of the right hind limb of each rat in Group 2-Group 7. The injection was performed from the anterior aspect of the knee joint, which was slightly extended and flexed. Sterile saline (0.05 mL) alone was injected into Group 1 rats.

Four hours after MSU administration, the rats were anesthetized, the diameter of right knee joints were measured with calipers; surface temperature for right knees were measured. Synovial lavage fluid from the knee was collected by injecting phosphate buffered saline with 1% BSA (0.2 mL) into the joint cavity, the fluid then collected, centrifuged and the supernatants stored at −80° C.

STEP C: Increase in Knee Diameter (mm)

Figure 7:
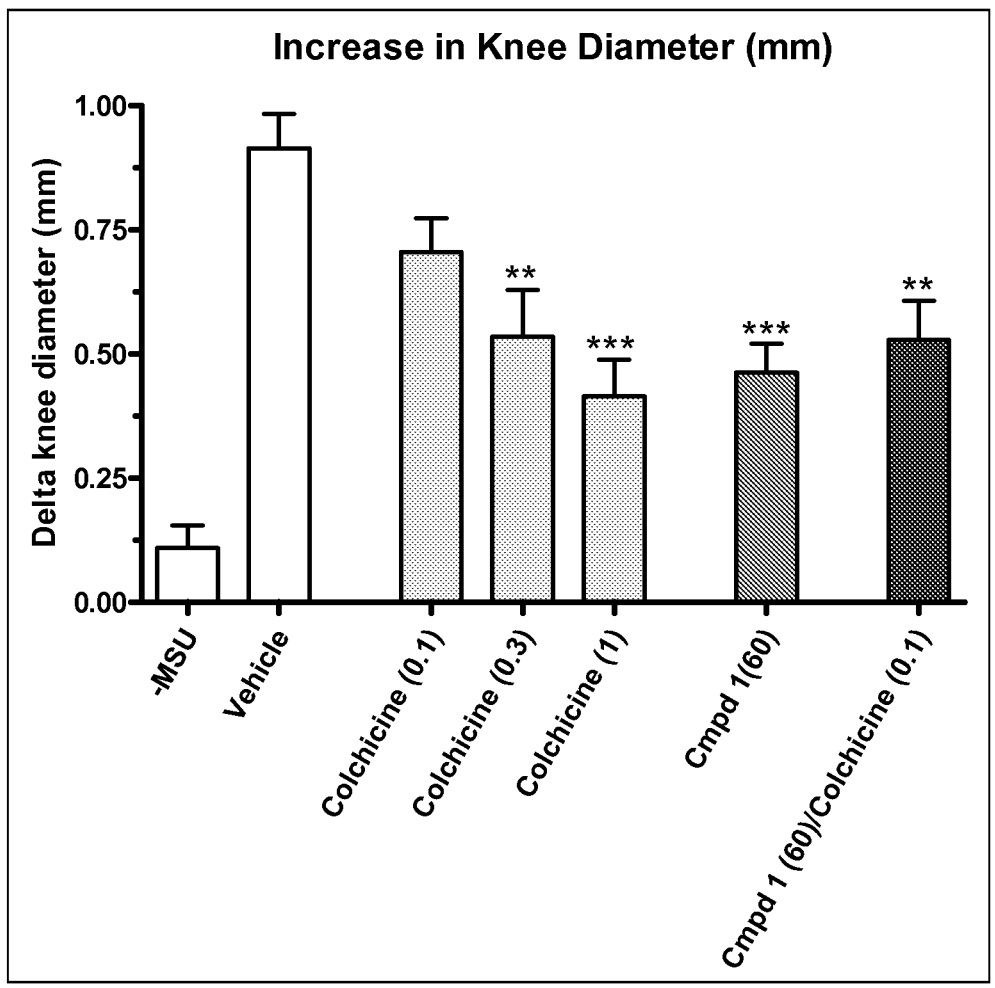
FIG. 7 illustrates the average increase in knee diameter (mm) in an in vivo MSU-induced rat knee joint study for various doses of colchicine s.c. (0.1, 0.3, 1 mg/kg), Lesinurad p.o. (60 mg/kg/day), and Lesinurad and colchicine ( indicates p<0.01 versus vehicle; * indicates p<0.001 versus vehicle).

The average increase in knee diameter (mm), which is used as a marker for MSU-induced knee joint swelling, is shown in Table 6 below for various doses of Lesinurad and/or colchicine and graphically in FIG. 7 (statistical analysis: One-way ANOVA followed by Dunnett's test), demonstrating

- Four hours post saline injection there was little change in the knee diameter from the pre-injection time;
- Increase in knee diameter after MSU injection was about nine fold compared to saline;
- Colchicine (0.1, 0.3 and 1mg/kg) dose-dependently decreased the MSU-induced increase in knee diameter;
- Lesinurad significantly decreased the MSU-induced increase in knee diameter;
- Lesinurad (60 mg/kg/day) co-administered with colchicine (0.1 mg/kg), did not significantly produce better efficacy than either therapy alone.

TABLE 6

Increase in Rat Knee Diameter

| Regimen | Dose mg/kg | n | Av |
|---|---|---|---|
| Control | | 10 | 0.11 |
| Vehicle | | 15 | 0.91 |
| Colchicine** | 0.1 | 10 | 0.71 |
| Colchicine*** | 0.3 | 10 | 0.53 |
| Colchicine*** | 1 | 15 | 0.41 |
| Lesinurad*** | 60 | 15 | 0.46 |
| Lesinurad/Colchicine** | 60/0.1 | 10 | 0.53 |

**p < 0.01 vs Vehicle;
***p < 0.001 vs Vehicle

III. Human Clinical Trials

Example 4

Phase II Clinical Trial—Gout Dose Response Study

Purpose: To compare the proportion of subjects whose serum urate (sUA) level is <6.0 mg/dL after 28 days of dosing by treatment group.

Official Title: Randomized, Double-Blind, Multicenter, Placebo-Controlled, Safety and Efficacy Study of Lesinurad Versus Placebo in the Treatment of Hyperuricemia in Patients With Gout Experimental dosage form: 200 mg capsule of Lesinurad, with appropriate pharmaceutically acceptable excipients Condition: Hyperuricemia
Intervention: Lesinurad or Placebo
Study Type: Interventional
Study: Allocation: Randomized
Design:
Control: Placebo Control
Endpoint Classification: Safety/Efficacy Study
Intervention Model: Parallel Assignment
Masking: Double Blind (Subject, Caregiver, Investigator, Outcomes Assessor)
Primary Purpose: Treatment
Primary Outcome Measures: Compare the proportion of subjects whose serum urate (sUA) level is <6.0 mg/dL after 28 days of dosing by treatment group.
Secondary Outcome Measures:
Evaluate the proportion of subjects with sUA levels <6.0 mg/dL at each weekly study visit.
Evaluate absolute and percent reduction from baseline in sUA levels at each weekly study visit.
Evaluate the percent change in 24-hr urine urate level (excretion) from baseline to Day 28.
Evaluate the incidence of gout flares.
Evaluate the safety and tolerability of Lesinurad in subjects with gout.

TABLE 7

Clinical Study Design

| Arm | Intervention |
|---|---|
| 1 | Lesinurad<br>200 mg qd for 28 days |
| 2 | Lesinurad<br>200 mg qd for 7 days followed by<br>400 mg qd for 21 days |
| 3 | Lesinurad<br>200 mg qd for 7 days, followed by<br>400 mg qd for 7 days, followed by<br>600 mg qd for 14 days |
| 4 | Matching placebo<br>qd for 28 days |

Eligibility
Ages Eligible for Study: 18-75 Years
Genders Eligible for Study: Both
Accepts Healthy Volunteers: No
Inclusion Criteria:
Male or post-menopausal or surgically sterile female.
Hyperuricemic (i.e., screening sUA≥8 mg/dL).
Meets criteria for the diagnosis of gout as per the American Rheumatism Association (ARA) Criteria for the Classification of Acute Arthritis of Primary Gout (see Appendix B).
Willing and able to give informed consent and adhere to visit/protocol schedules (informed consent must be given before the first study procedure is performed).
Exclusion Criteria:
Classified as an overproducer of urine urate (Cur>6.0 ml/min/1.73 m² 24-hour urine).
Consumes more than 14 drinks of alcohol per week (e.g., 1 drink=5 oz [150 ml] of wine, 12 oz [360 ml] of beer, or 1.5 oz [45 ml] of hard liquor).
History or suspicion of drug abuse.
Documented history of, or suspicion of, kidney stones.
History of rheumatoid arthritis or other autoimmune disease.
Confirmed (positive serology to HIV1 and HIV2) or suspected HIV infection.
Positive serology to HCV antibodies (Abs), and/or hepatitis B surface antigen (HBsAg).
History of malignancy, except treated non-melanomatous skin cancer or cervical dysplasia.
History of cardiac abnormalities, including abnormal and clinically relevant ECG changes such as bradycardia (sinus rate <45 bpm), complete left bundle branch block (LBBB), second or third degree heart block, intraventricular conduction delay with QRS duration >120 msec, symptomatic or asymptomatic arrhythmias with the exception of sinus arrhythmia, evidence of ventricular pre-excitation, frequent palpitations or syncopal episodes, heart failure, hypokalemia, family history of Long QT Syndrome, and/or family history of sudden death in an otherwise healthy individual between the ages of 1 and 30 years.
Any condition predisposing them to QT prolongation including pathological Q-wave (defined as Q-wave >40 msec or depth >0.4-0.5 mV).
Any use of a concomitant medication that prolong the QT/QTc interval within the 14 days prior to Baseline (Day 0).
QT interval corrected for heart rate according to Fridericia (QTcF)>450 msec at Screening or pre-dose at Baseline (Day 0).
Uncontrolled hypertension (above 150/95).
Inadequate renal function [serum creatinine>1.5 mg/dL or creatinine clearance<60 mL/min (by Cockroft-Gault formula)].
Hemoglobin<10 g/dL (males) or <9 g/dL (females).
Alanine aminotransferase (ALT) or aspartate aminotransferase (AST)>2.5×upper limit of normal (ULN).
Gamma glutamyl transferase (GGT)>3×ULN.
Active peptic ulcer disease requiring treatment.
History of xanthinuria, active liver disease, or hepatic dysfunction.
Requires therapy with any other urate-lowering medication, other than the study medication.
Requires long-term use of salicylates; diuretics; azathioprine; mercaptopurine; theophylline; intravenous colchicine; cyclosporine; cyclophosphamide; pyrazinamide; sulfamethoxazole; or trimethoprim.
Taking medications known as enzyme inducers.
Gout flare at screening that is resolved for less than one week prior to the first treatment with study medication (exclusive of chronic synovitis/arthritis).
Pregnant or breast feeding.
Received an investigational medication within 4 weeks prior to study medication administration.
Known hypersensitivity or allergy to colchicine or any components in their formulations.
Body mass index (BMI) >40 kg/m².
Taking greater than 1000 mg/day of Vitamin C.
Any other medical or psychological condition, which in the opinion of the Investigator and/or Medical Monitor, might create undue risk to the subject or interfere with the subject's ability to comply with the protocol requirements, or to complete the study.
Results: Incidence of gout flares are presented in Table 8 below indicating the majority of flares occurred in the first week when patients were receiving 200 mg QD (6/10 total flares on drug). Few additional flares occurred as dose increased, even with greater decrease in sUA. Duration of flares is shorter at higher doses, the opposite of what would be expected with greater reduction in sUA.

TABLE 8

Incidence of Gout Flares

| Randomized Dose Group | N | % Patients with Flares | Mean Duration of Flares | % of patients with Flares by Dose at Time of Flare | Mean Duration of Flares |
|---|---|---|---|---|---|
| 600 mg | 32 | 13% | 1.5 days | 9% (3/32) | 1.7 days |
| 400 mg | 33 | 12% | 3.8 days | 2% (1/65) | 2 days |
| 200 mg | 31 | 6% | 4 days | 6% (6/96) | 4 days |
| Placebo | 27 | 4% | 1 day | 4% | 1 day |

Example 5

Lesinurad Treatment of Gout Patients with Hyperuricemia

A phase II clinical trial including 123 gout patients with hyperuricemia (serum uric acid ≥8 mg/dL) in 4 treatment arms was conducted. The trail lasted 8 weeks, comprising a 2 week run in period, 4 week treatment period and 2 week follow-up.

Figure 8:
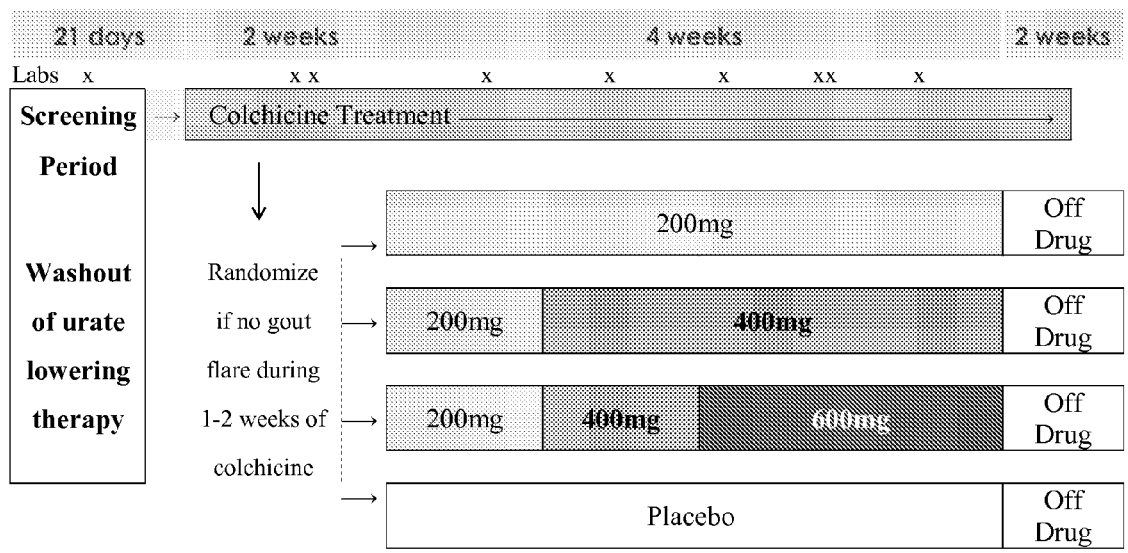
FIG. 8 illustrates the Phase II clinical study design for Lesinurad treatment of gout patients with hyperuricemia.

Patients were randomly assigned to arms 1, 2, 3 or 4 and orally administered Lesinurad according to Table 9 below and FIG. 8; all received colchicine prophylaxis (0.5-0.6 mg QD) for 2 weeks prior to Lesinurad dosing and throughout the 4 week treatment period.

TABLE 9

Clinical Study Design

| | | Lesinurad dose (mg) | | | |
|---|---|---|---|---|---|
| Arm | n | Week 1 | Week 2 | Week 3 | Week 4 |
| 1 | 31 | 200 | 200 | 200 | 200 |
| 2 | 33 | 200 | 400 | 400 | 400 |
| 3 | 32 | 200 | 400 | 600 | 600 |
| 4 | 27 | 0 (placebo) | 0 (placebo) | 0 (placebo) | 0 (placebo) |

Time to first flare for each arm is given in Table 10 below (indicating cumulative flare rate).

TABLE 10

Time to First Flare

| Arm | Day 0 | Day 7 | Day 14 | Day 21 | Day 28 |
|---|---|---|---|---|---|
| 1 | 27 | 27 | 26 | 25 | 25 |
| 2 | 31 | 31 | 30 | 28 | 26 |
| 3 | 33 | 31 | 31 | 29 | 29 |
| 4 (placebo) | 32 | 32 | 32 | 29 | 29 |

Table 11 below shows the percent of patients experiencing at least one gout flare by week 4 of treatment, calculated based on ITT patient number.

TABLE 11

Percent of Patient Experiencing at Least One Gout Flare by Week Four

| ARM | 4 Wk % Flare |
|---|---|
| 1 | 10 |
| 2 | 12 |
| 3 | 13 |
| [1]Placebo[2] | 12-22[3] |
| [1]Placebo[4] | 34 |

[1]Data from clinical studies APEX (Phase III) and TMX-00-004 (Phase II).
[2]Colchicine 0.6 mg qd, bid, or naproxen 250 mg qd administered prophylactically.
[3]Projected based on two times the 2 week flare data from TMX-00-004.
[4]TMX-0-004 study had 2 weeks on colchicine 0.6 mg bid, 2 weeks off during treatment period.

Figure 9:
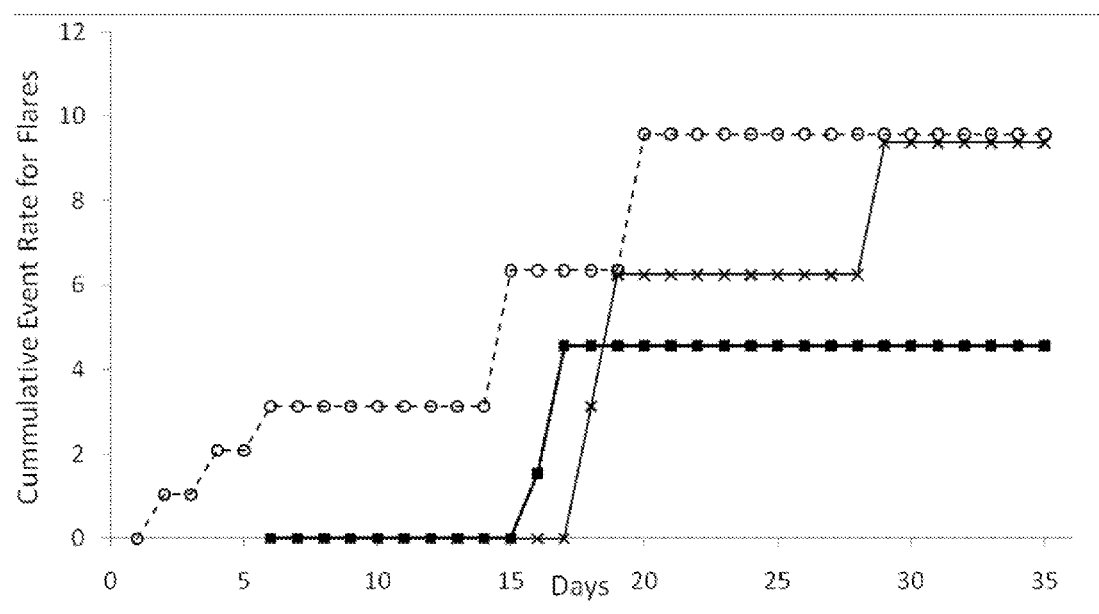
FIG. 9 illustrates the time to first flare compared to a published colchicine control. The actual dose at the time of flare is shown and only flares requiring treatment were considered.

FIG. 9 shows a plot of the cumulative flare rate for flares from days 0-35. In a separate study (see Schlesinger et at EULAR, 2010, Abstract OP 0198, "Efficacy of Canakinumab (ACZ885) in the Prevention of Flares in Gout Patients initiating Allopurinol Therapy") allopurinol dosed with colchicine (0.5 mg QD) resulted in 28% of patients experiencing flares.

What is claimed is:

1. A method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and colchicine to a subject, wherein the daily dose of 2-(5-bromo-4-(4-cyclopropylnaphthalen-1-yl)-4H-1,2,4-triazol-3-ylthio)acetate, or a pharmaceutically acceptable salt thereof, is about 400 mg or about 200 mg, and the dosage of colchicine is 0.3 mg to 1.2 mg.

2. The method of claim 1, wherein the daily dose of 2-(5-bromo-4-(4-cyclopropylnaphthalen-1-yl)-4H-1,2,4-triazol-3-ylthio)acetate, or a pharmaceutically acceptable salt thereof, is about 400 mg.

3. The method of claim 1, wherein the daily dose of 2-(5-bromo-4-(4-cyclopropylnaphthalen-1-yl)-4H-1,2,4-triazol-3-ylthio)acetate, or a pharmaceutically acceptable salt thereof, is about 200 mg.

4. The method of claim 2, wherein the daily dose is administered orally.

5. The method of claim 2, wherein the daily dose is administered in the morning.

6. The method of claim 2, wherein the daily dose is administered with food.

7. The method of claim 2, further comprising administration of a second serum uric acid lowering agent.

8. The method of claim 7, wherein the second serum uric acid lowering agent is a xanthine oxidase inhibitor.

9. The method of claim 8, wherein the xanthine oxidase inhibitor is febuxostat or allopurinol.

10. The method of claim 3, wherein the daily dose is administered orally.

11. The method of claim 3, wherein the daily dose is administered in the morning.

12. The method of claim 3, wherein the daily dose is administered with food.

13. The method of claim 3, further comprising administration of a second serum uric acid lowering agent.

14. The method of claim 13, wherein second serum uric acid lowering agent is febuxostat or allopurinol.

* * * * *